US012741032B2

(12) United States Patent
Hui et al.

(10) Patent No.: US 12,741,032 B2
(45) Date of Patent: Sep. 22, 2026

(54) ANTI-CLDN18.2 ANTIBODY, DRUG CONJUGATE, AND PREPARATION METHOD THEREFOR AND USE THEREOF

(71) Applicant: CSPC MEGALITH BIOPHARMACEUTICAL CO., LTD., Shijiazhuang (CN)

(72) Inventors: Xiwu Hui, Shijiazhuang (CN); Zhaopeng Sun, Shijiazhuang (CN); Weirong Cao, Shijiazhuang (CN); Bing Yao, Shijiazhuang (CN); Boning Liu, Shijiazhuang (CN); Xixin Hu, Shijiazhuang (CN); Can Yuan, Shijiazhuang (CN); Wenbin Li, Shijiazhuang (CN); Yancui Wang, Shijiazhuang (CN)

(73) Assignee: CSPC MEGALITH BIOPHARMACEUTICAL CO., LTD., Shijiazhuang (CN)

( * ) Notice: Subject to any disclaimer, the term of this patent is extended or adjusted under 35 U.S.C. 154(b) by 641 days.

(21) Appl. No.: 18/039,393

(22) PCT Filed: Nov. 26, 2021

(86) PCT No.: PCT/CN2021/133376

§ 371 (c)(1),
(2) Date: May 30, 2023

(87) PCT Pub. No.: WO2022/111616

PCT Pub. Date: Jun. 2, 2022

(65) Prior Publication Data

US 2023/0414774 A1 Dec. 28, 2023

(30) Foreign Application Priority Data

Nov. 30, 2020 (CN) ........................ 202011385844.4

(51) Int. Cl.

| | |
|---|---|
| ***C07K 16/28*** | (2006.01) |
| ***A61K 31/4745*** | (2006.01) |
| ***A61K 31/537*** | (2006.01) |
| ***A61K 45/06*** | (2006.01) |
| ***A61K 47/68*** | (2017.01) |

(52) U.S. Cl.

CPC ...... *A61K 47/6803* (2017.08); *A61K 31/4745* (2013.01); *A61K 31/537* (2013.01); *A61K 45/06* (2013.01); *C07K 16/28* (2013.01)

(58) Field of Classification Search

None

See application file for complete search history.

(56) References Cited

U.S. PATENT DOCUMENTS

| | | | | |
|---|---|---|---|---|
| 11,541,127 | B2 | 1/2023 | Sahin et al. | |
| 2017/0281711 | A1* | 10/2017 | Kumar | C07K 16/2863 |
| 2018/0117174 | A1* | 5/2018 | Sahin | A61K 47/6863 |
| 2022/0041712 | A1* | 2/2022 | Li | C07K 16/28 |
| 2022/0235128 | A1 | 7/2022 | Qu et al. | |

FOREIGN PATENT DOCUMENTS

| | | | |
|---|---|---|---|
| CN | 111777681 | A | 10/2020 |
| CN | 111944048 | A | 11/2020 |
| JP | 2018-513146 | A | 5/2018 |
| WO | WO 2020/160560 | A2 | 8/2020 |
| WO | WO 2022/007808 | A1 | 1/2022 |

OTHER PUBLICATIONS

Almagro, Frontiers in Immunology, 2018:8, 1751.*
Sela-Culang (Frontiers in Immunology, 2013, 4:302).*
Chiu (Antibodies, 2019, 8(55):1-80).*
Ni (The Protein Journal, 2024, 43:683-696).*
Janeway, Immuno Biology the immune system in Health and Disease, 4 edition, 1999, pp. 195-209.*
Wijesuriya et al. (Protein Expression and Purification, 2018, 149:75-83).*
Zhang (Chinese Journal of Cancer Research, 2020;32(2):263-270).*
China National Intellectual Property Administration, International Search Report and Written Opinion issued in International Patent Application No. PCT/CN2021/133376, mailed on Jan. 24, 2022.

* cited by examiner

*Primary Examiner* — Julie Wu

(74) *Attorney, Agent, or Firm* — Leydig, Voit & Mayer, Ltd.

(57) ABSTRACT

The present application provides an anti-CLDN18.2 antibody and an antibody-drug conjugate prepared from the antibody. The antibody or the antibody-drug conjugate can effectively treat CLDN18.2 positive tumors, comprising but not limited to cancers represented by gastric cancer and pancreatic cancer.

14 Claims, 15 Drawing Sheets

Specification includes a Sequence Listing.

| $EC_{50}$ | ng/ml |
|---|---|
| SYJS001 mAb | 131.8 |

| $EC_{50}$ | ng/ml |
|---|---|
| SYJS001 mAb | 149 |
| SYJS001 ADC | 133 |

| ADC | $ED_{50}$ (ng/ml) |
| --- | --- |
| SYJS001 ADC | 20.8 |
| IMAB362 ADC | 43.01 |

| | 0 hr | 4 hr | 21 hr | 25 hr | 48hr |
|---|---|---|---|---|---|
| IMAB362 ADC | 0.0 | 35.8 | 89.2 | 92.4 | 98.1 |
| SYJS001 ADC | 0.0 | 58.1 | 89.4 | 92.0 | 99.2 |

| ADC | $IC_{50}$ (ng/ml) |
|---|---|
| SYJS001-ADC | 29.9 |
| IMAB362-ADC | 63.3 |

| ADC | $IC_{50}$ (ng/ml) |
|---|---|
| SYJS001-ADC | 293.5 |
| IMAB362-ADC | 1662.0 |

ANTI-CLDN18.2 ANTIBODY, DRUG CONJUGATE, AND PREPARATION METHOD THEREFOR AND USE THEREOF

CROSS-REFERENCE TO RELATED APPLICATIONS

The present application is the U.S. national stage of PCT/CN2021/133376, filed Nov. 26, 2021, which claims priority to Chinese Patent Application No. 202011385844.4, filed on Nov. 30, 2020, titled "ANTI-CLDN18.2 ANTIBODY-DRUG CONJUGATE, AND PREPARATION METHOD THEREFOR AND USE THEREOF", each of which is incorporated herein by reference in its entirety for all purposes.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 14,598 byte ASCII (Text) file named "767591_ST25.txt", created on May 26, 2023.

TECHNICAL FIELD

The present application generally relates to the field of biomedicine, and more particularly to anti-CLDN18.2 antibodies, related conjugates (e.g., antibody-drug conjugates) and their use in the treatment or prevention of tumors.

BACKGROUND

Tight junctions (TJs) are important functional components of normal epithelial cell-to-cell adhesion. They mechanically connect cells to form epithelial barriers, prevent macromolecular transport between cells, and maintain epithelial cell polarity. The proteins constituting tight junctions are mainly Claudin (also referred to as occlusive protein, sealant protein, tight junction protein, etc., and for avoiding any ambiguity, referred to as Claudin or the abbreviation CLDN in the present application), Occludin, ZO-1, ZO-2, ZO-3, cingulin, Pals1 and MUPP1, among which Claudin and Occludin are the most critical proteins.

Claudin is a backbone protein that makes up tight junctions, and its aberrant expression can lead to structural destruction and impaired function of epithelial cells and endothelial cells, and may play an important role in the pathogenesis of various diseases. To date, it has been found that the Claudin gene family includes 24 members and that members are functionally highly conserved in evolution. The molecular mass of Claudin is 22-27 kD. Each Claudin molecule has the same structure. Claudin is widely distributed in normal tissues and different tumor tissues with differential expressions. Several type of Claudin were found to have abnormal expressions in precancerous lesions of gastric cancer and gastric cancer, which are associated with prognosis.

Humanized Claudin18 gene has two different first exons, and therefore can generate two splice variants Claudin18.1 (hereinafter referred to as CLDN18.1) and Claudin18.2 (hereinafter referred to as CLDN18.2). The amino acid sequences of human CLDN18.1 and 18.2 are both 261 amino acid residues in length, and they have 21 different amino acid residues at positions 0-70. When the two subtypes of CLDN18 are transcriptionally amplified in different tissues, it was found that CLDN18.1 was selectively expressed in cells of normal lungs, while the expression of CLDN18.2 in normal stomachs was limited to differentiated short-lived gastric epithelial cells.

Scientific studies have shown that although CLDN18.1 and CLDN18.2 are very structurally similar, their expressions in tumors are quite different. For example, for normal tissues, CLDN18.1 is expressed only in lungs, while CLDN18.2 is limitedly expressed in stomachs. For tumor tissues, CLDN18.1 is not significantly overexpressed in lungs, whereas CLDN18.2 is upregulated in cancers such as gastric cancer, esophageal cancer, and pancreatic cancer. When malignant transformation of gastric epithelium occurs, a disorder in cell polarity results in exposure of CLDN18.2 epitopes on cell surfaces. At the same time, CLDN18.2 gene is abnormally activated, highly selectively and stably expressed in specific tumor tissues, and involved in the proliferation, differentiation and migration of tumor cells, which makes CLDN18.2 an effective molecular target for potential antineoplastic drugs.

The worldwide annual incidence rate of gastric cancer is 13.86/100,000. A large proportion of patients have reached the advanced stage at the time of diagnosis, and their recovery after surgery is very unsatisfactory. In addition, the incidence rate of the elderly is high. The overall average survival time is shorter than one year, and the 5-year survival rate is less than 20%.

Pancreatic cancer is also one of the most malignant tumors currently, with a median survival time of less than 6 months and a 5-year overall survival rate of less than 6%.

Research and development of antineoplastic drugs targeting CLDN18.2 has been under way worldwide. Currently, there are many (about 28) projects targeting CLDN18.2, including monoclonal antibodies, bispecific antibodies, and CAR-T targeting CLDN18.2. Among all the projects, the most developed is monoclonal antibody Claudiximab (now under the name of Zolbetuximab) from Ganymed, Inc. (incorporated by Astellas). Its clinical trial for the indication of gastric cancer has entered phase III. A total of 9 projects entered clinical phases, and most other projects are in pre-clinical phases. There was considerable uncertainty about the therapeutic effects. Based on the current data, no clinical study of antibody-drug conjugates (ADCs) targeting CLDN18.2 has been reported.

CLDN18.2 is an excellent target for the treatment of digestive tract cancers and pancreatic cancers. However, CLDN18.1 differs from CLDN18.2 by 7 amino acid residues in the extracellular domain ECD1 of about 50 amino acids, and therefore how to design an antibody that specifically recognizes CLDN18.2 but not CLDN18.1 is a challenge in drug development of monoclonal antibodies targeting CLDN18.2.

Furthermore, although monoclonal antibody therapies generally have the characteristics including high target specificity and low side effect, a monoclonal antibody's efficacy alone is limited. Thus, most monoclonal antibodies are used in combination with chemotherapeutic agents. Currently, the main approach to enhance the efficacy of monoclonal antibodies is use of antibody-drug conjugates. Antibody-drug conjugates belong to a new class of anticancer biological missile drugs, consisting essentially of three elements, i.e., antibodies, drug molecules, and linkers connecting antibodies with drug molecules. Upon conjugating monoclonal antibodies to drug molecules by chemical coupling, antibody-drug conjugates specifically recognize an receptor targeted by the antibody on the surface of an cancer cell by means of the targeting capability of the monoclonal antibody, bind to the receptor, enter the cell, release the drug molecules via cleavage by intracellular proteases, and therefore prevent the cancer cell from multiplying and kill the cancer cell. The antibody-drug coupling technique integrates small molecule drugs with biological proteins, which makes use of their advantages, enhances drug efficacy and reduces toxic and side effects. ADCs become a new generation of therapeutic products.

As of September 2020, a total of 9 ADC drugs were approved for marketing by the FDA, including Adcetris from Seattle, Kadcyla and Polivy from Genentech, Besponsa and Mylotarg from Wyeth, Lumoxiti and Enhertu from AstraZeneca, and Trodelvy from immunomedics. No ADC drug developed in China have been marketed.

Both antibody drugs and antibody-drug conjugates are promising types of drugs. More comprehensive research and development is urgently needed in the medical field of.

SUMMARY

In a first aspect, there is provided in the present application a conjugate comprising an anti-CLDN18.2 antibody or an antigen-binding fragment of the antibody of the present application conjugated with one or more drug molecules.

In a second aspect, there is provided in the present application a pharmaceutical composition comprising the conjugate of the first aspect and a pharmaceutically acceptable carrier.

In a third aspect, there is provided in the present application use of the conjugate of the first aspect or the pharmaceutical composition of the second aspect in the manufacture of a medicament for the treatment or prevention of cancer.

In a fourth aspect, there is provided in the present application a method of treating cancer in a subject, comprising administering to the subject suffering from the cancer a therapeutically effective amount of the conjugate of the first aspect or the pharmaceutical composition of the second aspect.

In a fifth aspect, there is provided in the present application a medical preparation (e.g., a kit) comprising the conjugate of the first aspect or the pharmaceutical composition of the second aspect.

In a sixth aspect, there is provided in the present application use of the conjugate of the first aspect and an antiproliferative agent in the manufacture of a medicament for the treatment of a tumor.

In a seventh aspect, there is provided in the present application a pharmaceutical composition comprising the conjugate of the first aspect and an antiproliferative agent.

In an eighth aspect, there is provided in the present application a method of treating a tumor in a subject, comprising administering to the subject suffering from the tumor a therapeutically effective amount of the conjugate of the first aspect or the pharmaceutical composition of the second aspect and an antiproliferative agent.

In a ninth aspect, there is provided in the present application an anti-CLDN18.2 antibody or an antigen-binding fragment of the antibody, a pharmaceutical composition comprising the antibody or antigen-binding fragment, use of the antibody or antigen-binding fragment in the manufacture of a medicament, and a method of using the antibody or antigen-binding fragment to treat a tumor/cancer.

CLDN18.2, where group 1 denotes SYJS001 ADC (square dots), and group 2 denotes SYJS001 naked antibody (circle dots).

Figure 18:
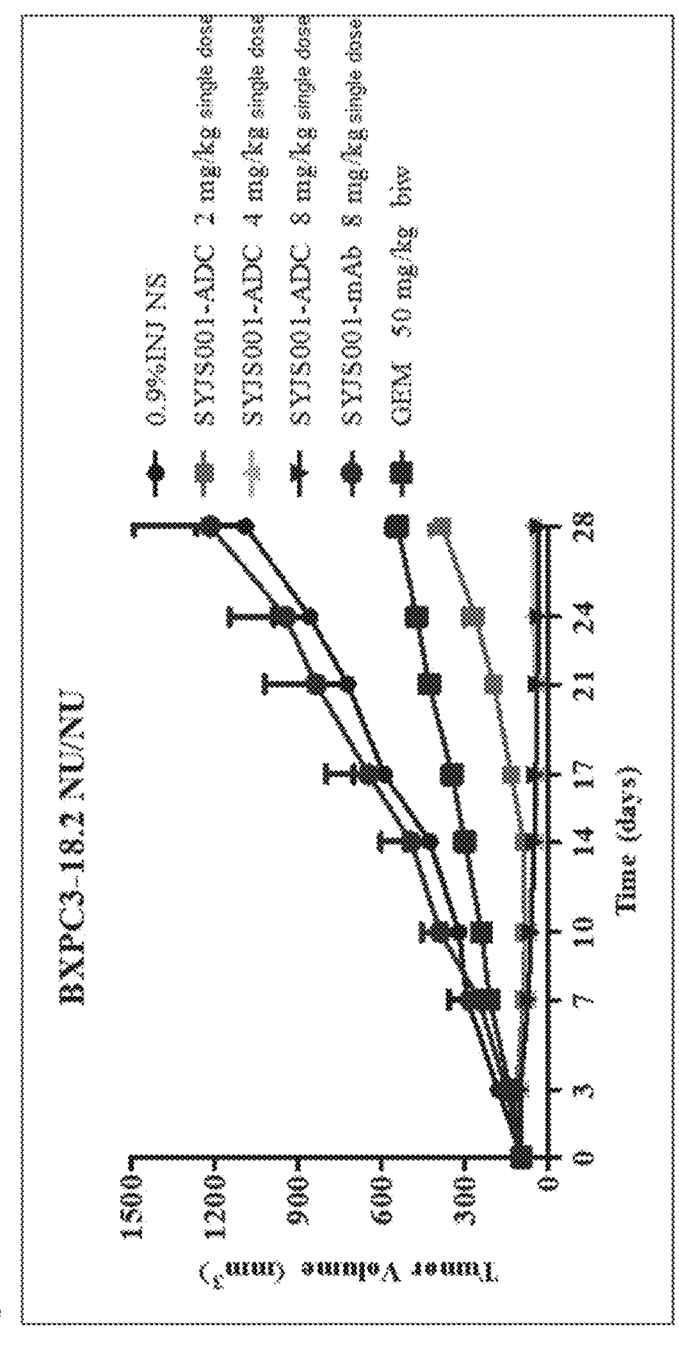

FIG. 18 shows the in vivo anti-tumor effect of SYJS001 ADC on BxPC-3-CLDN18.2 compared to gemcitabine.

Figure 19:
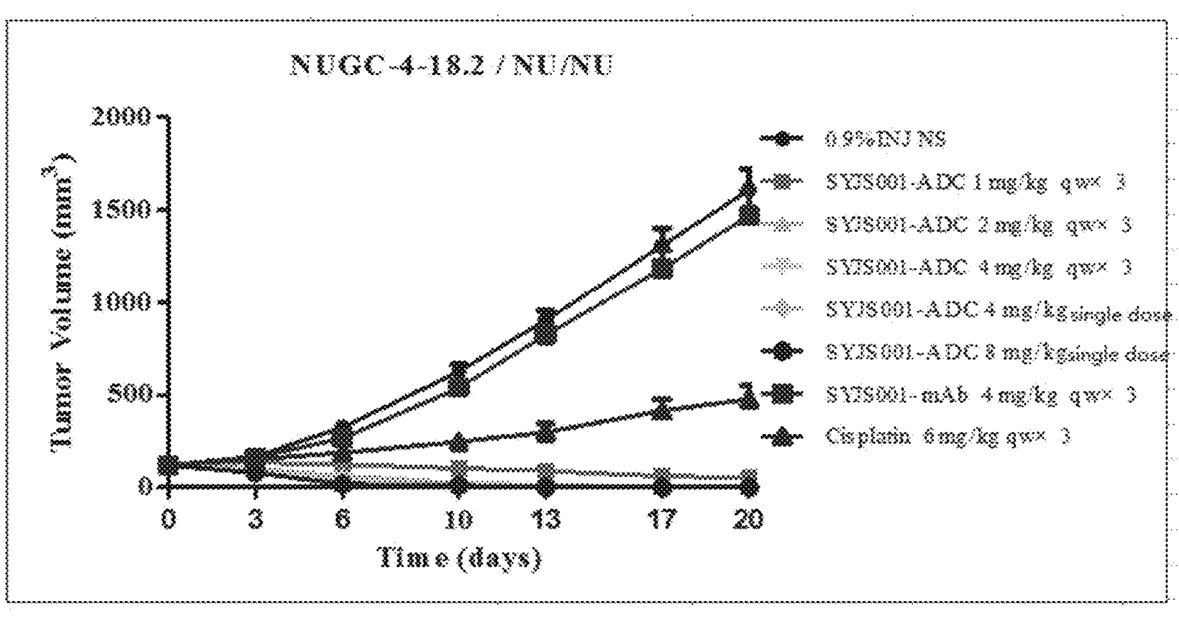

FIG. 19 shows the in vivo anti-tumor effect of SYJS001 ADC on NUGC4-CLDN18.2 compared to cisplatin.

Figure 20:
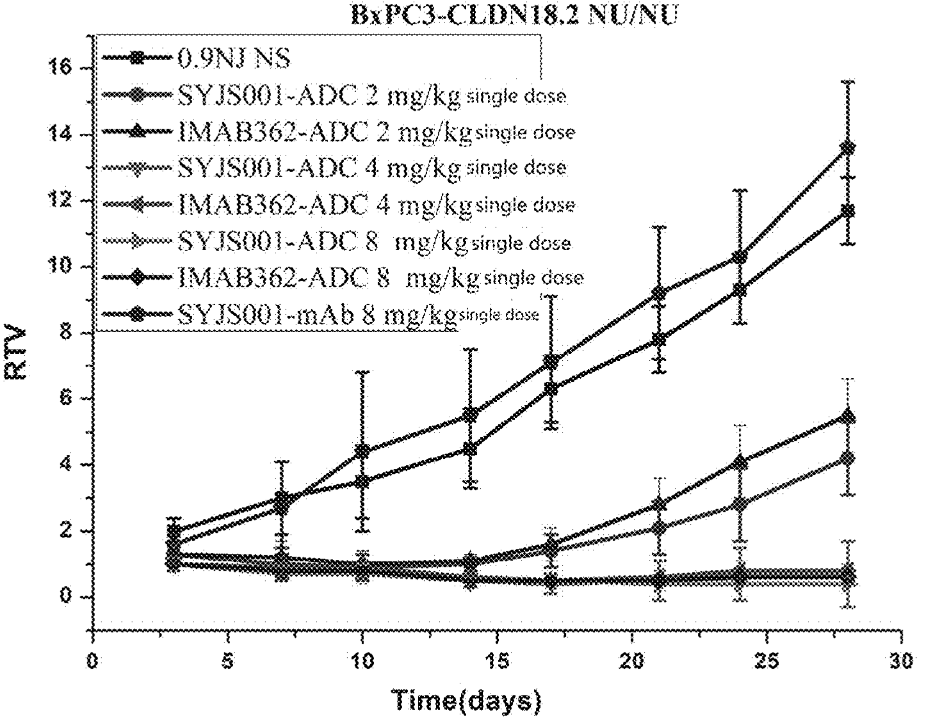

FIG. 20 shows the in vivo anti-tumor effect of SYJS001 ADC on BxPC-3-CLDN18.2 compared to IMAB362-ADC.

Figure 21:
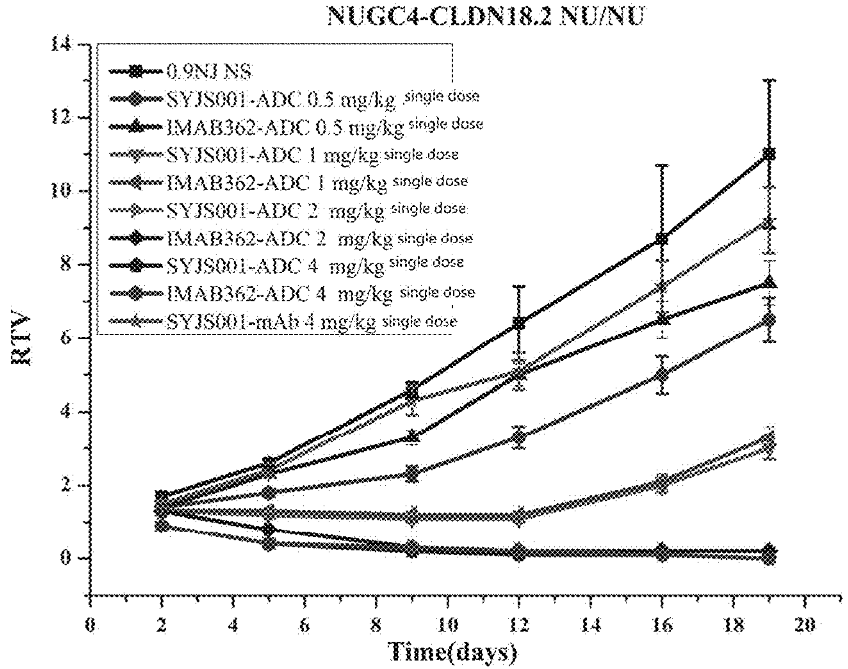

FIG. 21 shows the in vivo anti-tumor effect of SYJS001 ADC on NUGC4-CLDN18.2 compared to IMAB362-ADC.

Figure 22:
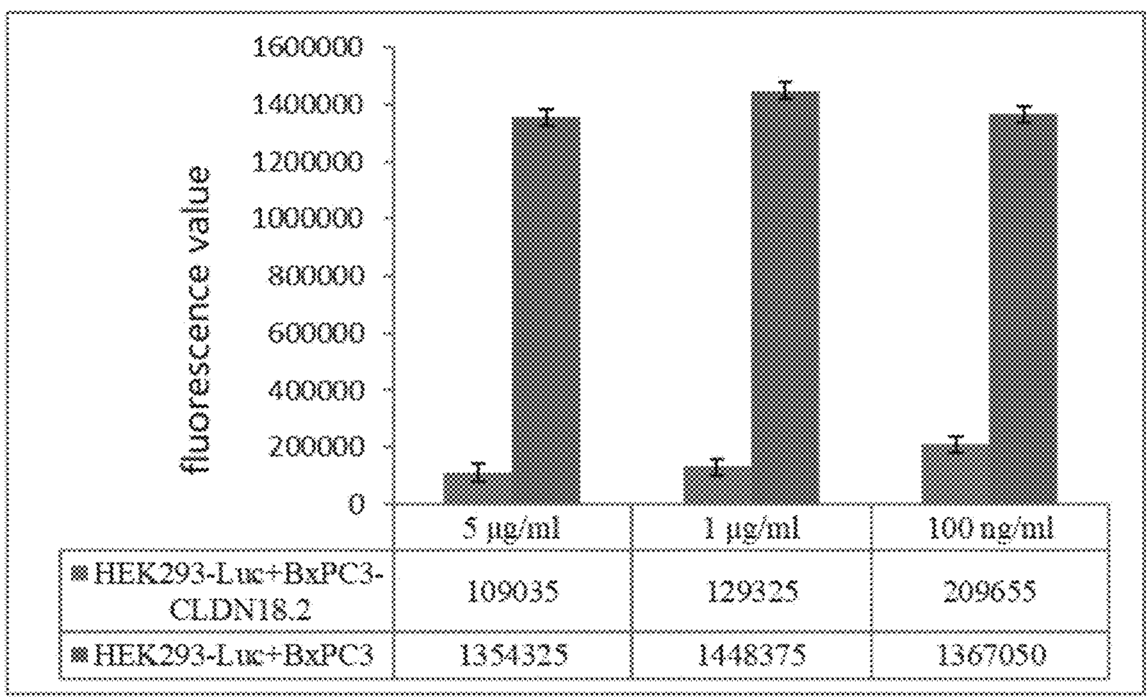

FIG. 22 shows the results of MMAE release versus bystander effect experiments.

Figure 23:
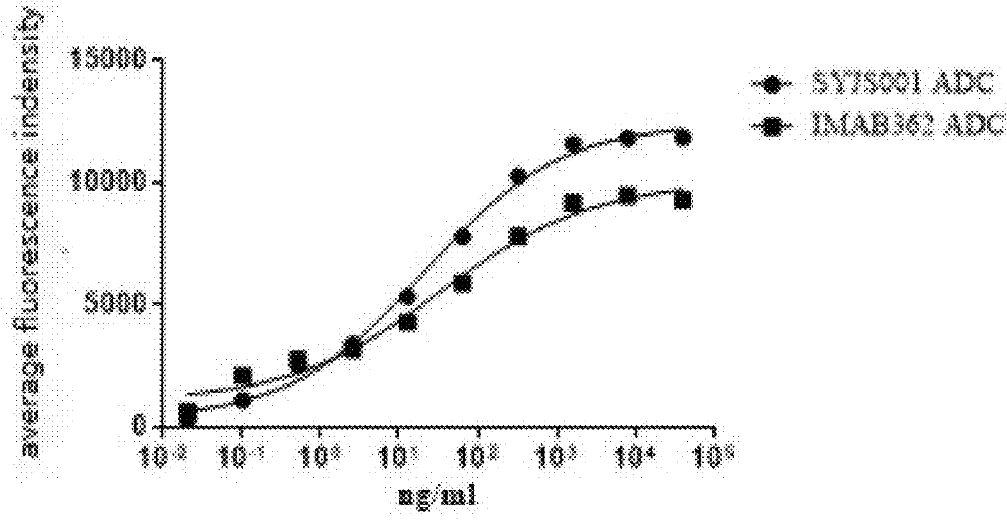

FIG. 23 shows the experimental results from affinity comparison between SYJS001 and IMAB362.

Figure 24:
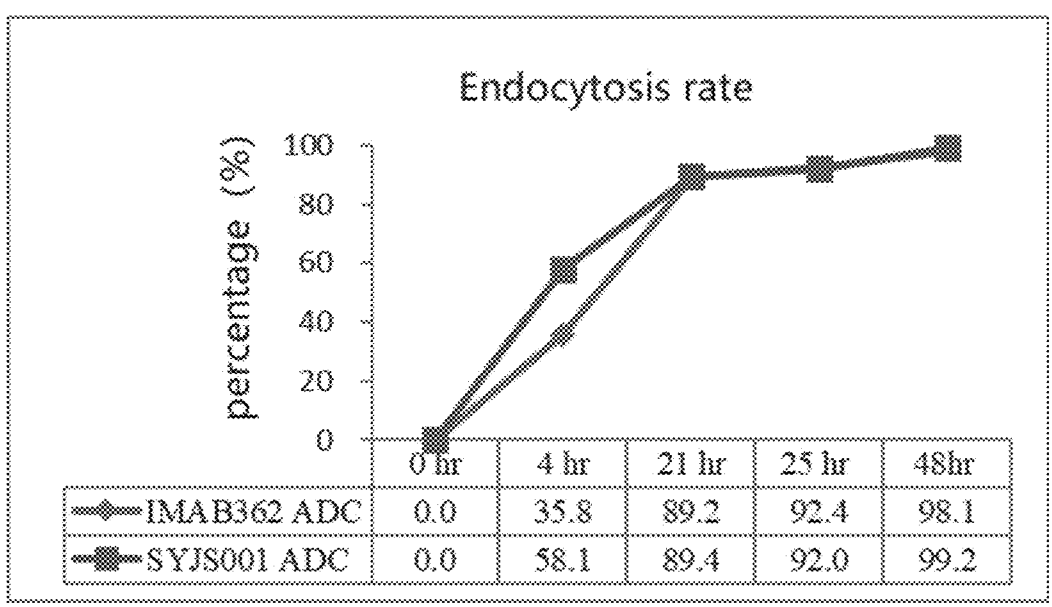

FIG. 24 shows the experimental results from endocytosis rate comparison between SYJS001 and IMAB362.

Figure 25:
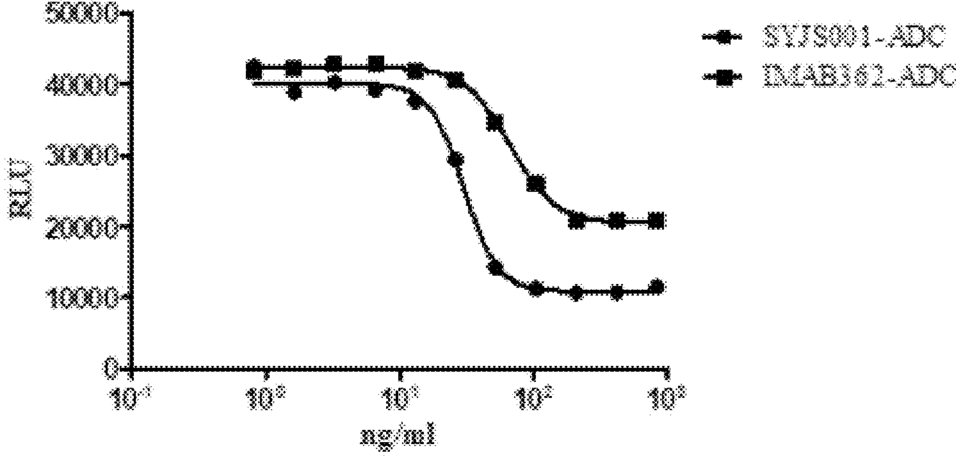

FIG. 25 shows the results of in vitro inhibition of cells by SYJS001 ADC and IMAB362 ADC (adenocarcinoma cell model).

Figure 26:
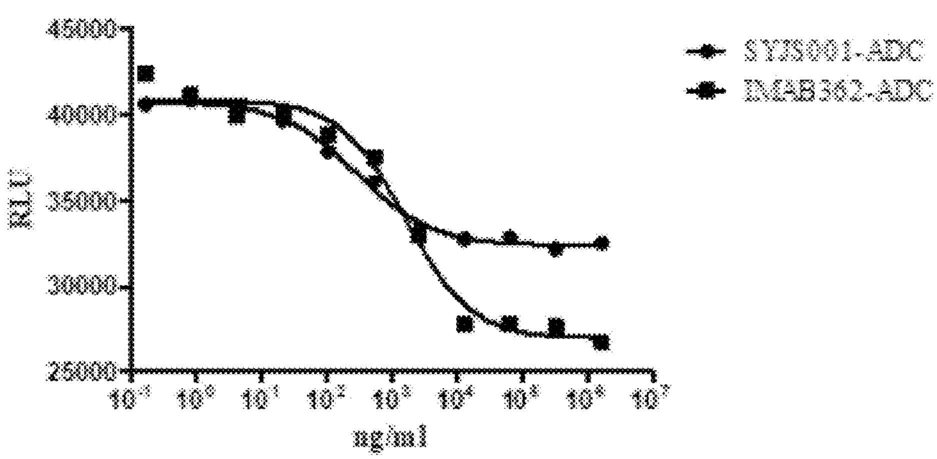

FIG. 26 shows the results of in vitro inhibition of cells by SYJS001 ADC and IMAB362 ADC (gastric cancer cell model).

DETAILED DESCRIPTION OF THE INVENTION

Definition

Unless defined otherwise, all scientific and technical terms used herein have the same meaning as understood by one of ordinary skill in the art. For definitions and terms in the art, a person skilled in the art may refer specifically to Current Protocols in Molecular Biology (Ausubel). Abbreviations for amino acid residues are standard 3-letter and/or 1-letter codes used in the art to refer to one of the 20 common L-amino acids.

Although the numerical ranges and parameter approximations are shown in broad ranges in the present application, the numerical values shown in the specific embodiments are described as accurately as possible. However, any numerical values inherently contain certain errors due to the standard deviation present in their respective measurements. Additionally, all ranges disclosed herein are to be understood as encompassing any and all subranges contained therein. For example, a range of "1 to 10" should be considered to encompass any and all subranges between the minimum value of 1 and the maximum value of 10, inclusive, i.e., all subranges starting with a minimum value of 1 or more, such as 1 to 6.1, and subranges ending with a maximum value of 10 or less, such as 5.5 to 10. Additionally, any reference referred to as "incorporated herein" is to be understood as being incorporated in its entirety.

As used herein, the terms "pharmaceutical composition," "combinational drug," and "pharmaceutical combination" can be used interchangeably to denote a combination of at least one drug and, optionally, a pharmaceutically acceptable carrier or adjuvant that is combined together to achieve a particular purpose. In certain embodiments, the pharmaceutical composition includes a combination that is temporally and/or spatially separated, so long as it is capable of acting together to achieve the purpose of the present application. For example, the ingredients contained in the pharmaceutical composition (e.g., antibodies, nucleic acid molecules, nucleic acid molecule combinations and/or conjugates according to the present application) may be administered to a subject together or separately. When the ingredients contained in the pharmaceutical composition are separately administered to a subject, the ingredients may be administered to the subject simultaneously or sequentially. Preferably, the pharmaceutically acceptable carrier is water, a buffered aqueous solution, an isotonic salt solution such as PBS (phosphate buffer), glucose, mannitol, dextrose, lactose, starch, magnesium stearate, cellulose, magnesium carbonate, 0.3% glycerol, hyaluronic acid, ethanol, or polyalkylene glycols such as polypropylene glycol, or triglycerides. The type of a pharmaceutically acceptable carrier depends, inter alia, on whether the composition according to the present application is formulated for oral, nasal, intradermal, subcutaneous, intramuscular or intravenous administration. The compositions according to the present application may comprise wetting agents, emulsifying agents or buffer substances as additives.

The pharmaceutical compositions, vaccines or pharmaceutical formulations according to the present application may be administered by any suitable route, for example orally, nasally, intradermally, subcutaneously, intramuscularly or intravenously.

As used herein, "a therapeutically effective amount" or "an effective amount" refers to a dose sufficient to show benefit to a subject being administered. The actual administration dose, rate and course will depend on the condition and disease severity of the subject to be treated. The therapeutic prescription (e.g., prescribed dose) is ultimately the responsibility of and dependent on the general practitioner or other physicians, and generally takes into account the disease being treated, the condition of individual patient, the delivery site, the administration method, and other factors known to a physician.

As used herein, the term "subject" refers to mammal, such as human, as well as other animals, such as wild animals (e.g., herons, storks, or cranes), domestic animals (e.g., ducks, or geese), or experimental animals (e.g., gorillas, monkeys, rats, mice, rabbits, guinea pigs, woodchucks, or ground squirrels).

The term "antibody", in its broad sense, encompasses intact antibodies and any antigen-binding fragments ("antigen-binding moieties") or single chain versions thereof "Full length/intact antibody" refers to a protein comprising at least two heavy (H) chains and two light (L) chains interconnected by disulfide bonds. Each heavy chain contains a heavy chain variable region (VH) and a heavy chain constant region containing three domains CH1, CH2 and CH3. Each light chain contains a light chain variable region (VL) and a light chain constant region containing one domain CL. The VH and VL regions can be further divided into a plurality of regions with high variability, referred to as complementarity determining regions (CDRs). Among CDRs, there are more conservative regions referred to as framework regions (FRs). Each VH or VL consists of three CDRs and four FRs arranged from the amino terminus to the carboxy terminus in the following order: FR1, CDR1, FR2, CDR2, FR3, CDR3, and FR4. These variable regions of heavy and light chains contain binding domains that interact with antigens. The constant region of an antibody can mediate binding of immunoglobulins to tissues or factors in hosts, including various cells of the immune system (e.g., effector cells) and the first component of the classical complement system (Clq). Chimeric or humanized antibodies are also encompassed by antibodies according to the present application. A full-length/intact antibody may be any type of antibodies, such as IgD, IgE, IgG, IgA or IgM antibodies (or subclasses of the above), but not belonging to any particular class. Immunoglobulins can be assigned to different classes depending on the amino acid sequences of the heavy chain constant domain of antibodies. Generally, immunoglobulins have five main classes, i.e., IgA, IgD, IgE, IgG and IgM. Several of these classes can be further classified into subclasses (isotypes), such as IgG1, IgG2, IgG3, IgG4, IgA1 and IgA2. Heavy chain constant domains corresponding to various classes of immunoglobulins are referred to as α, δ, ε, γ and μ, respectively. Subunit structures and three-dimensional structures of various classes of immunoglobulins are well known.

Complementarity determining regions (CDRs, typically including CDR1, CDR2 and CDR3) are the subregions in variable regions that most impact on the affinity and specificity of an antibody. CDR sequences in a VH or VL can be defined in multiple common ways, including IMGT, the Chothia definition, and the Kabat definition. For a variable region sequence of a given antibody, the CDR sequences in the VH and VL sequences can be defined according to IMGT, the Chothia definition, or the Kabat definition.

The term "humanized antibody" refers to an antibody that may comprise CDR regions derived from a non-human antibody, and rest parts derived from one (or several) human antibodies. Moreover, in order to retain binding affinity, some residues of the backbone segments (referred to as FR) can be modified. Humanized antibodies or fragments thereof according to the present application can be prepared by techniques known to those skilled in the art.

The term "semi-humanized antibody" is defined in relation to a humanized antibody or a fully humanized antibody, and refers to an antibody which has a chain comprising a murine variable region (as in a chimeric antibody) and another chain comprising a humanized variable region.

The term "chimeric antibody" refers to an antibody in which the variable region sequence is from one species and the constant region sequence is from another species, e.g., an antibody in which the variable region sequence is from a mouse antibody and the constant region sequence is from a human antibody. Chimeric antibodies or fragments thereof according to the present application can be prepared by using genetic recombination techniques. For example, a chimeric antibody may be produced by cloning a recombinant DNA comprising a promoter and a sequence encoding a variable region of a non-human, particularly murine, monoclonal antibody according to the present application, and a sequence encoding a constant region of a human antibody. Chimeric antibodies of the present application encoded by such recombinant genes will be, for example, a murine-human chimera, and its specificity is determined by the variable regions derived from murine DNA and its isoforms are determined by the constant regions derived from human DNA. For a method of preparing a chimeric antibody, guidelines can be found in, for example, Verhoeyn et al. (BioEssays, 8: 74, 1988).

The term "monoclonal antibody" refers to a preparation of antibody molecules having same molecular compositions. Monoclonal antibody compositions exhibit a single binding specificity and affinity for a particular epitope.

The term "bispecific antibody" refers to an antibody having binding capacities for two antigenic epitopes. The two epitopes may be on different antigens or on a same antigen. Bispecific antibodies may have a variety of structural configurations. For example, a bispecific antibody may consist of two Fc fragments and two binding moieties fused thereto, respectively (similar to a native antibody, except that the two arms bind different antigen targets or epitopes). The antigen binding moiety may be a single chain antibody (scfv) or a Fab fragment.

As used herein, the term "antigen-binding fragment" refers in particular to antibody fragments such as Fv, scFv (sc denotes single chain), Fab, $F(ab')_2$, Fab', scFv-Fc fragment or diabody, or any fragment which is capable of increasing the half-life by chemical modification or by incorporation into liposomes, such as addition of poly(alkylene)glycols, such as polyethylene glycol ("pegylated") (referred to as pegylated fragments Fv-PEG, scFv-PEG, Fab-PEG, $F(ab')_2$-PEG or Fab'-PEG) ("PEG" represents polyethylene glycol). An antigen-binding fragment of an anti-CLDN18.2 antibody of the present application has CLDN18.2 binding activity. For example, an antigen-binding fragment consists of or comprises a partial sequence of the heavy or light chain variable region of the antibody from which it is derived. The partial sequence is sufficient to retain the same binding specificity and sufficient affinity as the antibody from which it is derived, and may comprise at least 5 amino acids, preferably 10, 15, 25, 50 and 100 contiguous amino acids of the antibody sequence from which it is derived.

Examples of antigen-binding fragments include, but are not limited to, (1) Fab fragments, which may be monovalent fragments having VL-CL chains and VH-CH1 chains; (2) $F(ab')_2$ fragments, which may be divalent fragments having two Fab' fragments linked by disulfide bridges of the hinge region (i.e., dimers of Fab'); (3) Fv fragments having VL and VH domains from a single arm of an antibody; (4) single chain Fv (scFv), which may be a single polypeptide chain consisting of a VH domain and a VL domain via a peptide linker; and (5) $(scFv)_2$, which may comprise two VH domains linked by a peptide linker and two VL domains that are combined with the two VH domains via disulfide bridges.

The terms "Fc fragment", "Fc domain", "Fc moiety" or the like refer to a portion of the constant region of an antibody heavy chain, including the hinge region, the CH2 fragment and CH3 fragment of the constant region.

Generally, in order to prepare a monoclonal antibody or an antigen-binding fragment thereof, in particular a murine monoclonal antibody or an antigen-binding fragment thereof, guidelines can be found in the techniques described in "Antibodies" manual (Harlow and Lane, Antibodies: A Laboratory Manual, Cold Spring Harbor Laboratory, Cold Spring Harbor NY, pp. 726, 1988) or techniques for preparing a monoclonal antibody from hybridoma cells described by Kohler and Milstein (Nature, 256: 495-497, 1975).

According to the structural information of a given anti-CLDN18.2 monoclonal antibody in the present application, the monoclonal antibody can be prepared in CHO-K1 cells (ATCC Number: CCL-61, Lot No.: 59965043) using methods known in the art.

The term "homology/identity" in the context of an amino acid or nucleic acid sequence is defined as the percentage of identical residues in an amino acid or nucleotide sequence variant that, after alignment and introduction of gaps, achieves maximum percent homology, if desired. Methods and computer programs for alignment are well known in the art.

The term "specific binding" refers to a non-random binding reaction between two molecules, such as binding of an antibody to an antigenic epitope.

The inventors of the present application first obtained an anti-CLDN18.2 monoclonal antibody which bound to CLDN18.2 on CLDN18.2 positive cells, mediated highly efficient internalization and was well suited for the development of ADCs. In subsequent ADC development, the inventors of the present application found that superior stability of conjugation of the linker and the drug molecule was achieved using $NH_2$-$PEG_3$-Val-Cit as the linker, whereby the humanized antibody was conjugated via the linker to a small molecule drug (e.g., MMAE), and the ADC drug obtained achieved a very strong killing effect on CLDN18.2-overexpressing cancer cells, particularly pancreatic cancer, gastric cancer and lung cancer cells, and had good stability. In particular, in vivo experiments showed that intravenous administration of the antibody-drug conjugate in nude mice with CLDN18.2-positive gastric or pancreatic tumor xenografts resulted in tumor growth inhibition in a dose-dependent way. Significant therapeutic effects were observed at single-dose intravenous administration of about 1 to 8 mg/kg. The best therapeutic effect was observed at 8 mg/kg. Individuals showed good tolerance. The overall therapeutic effect was significant. The ADC drug obtained in the present application could lead to a bystander effect, which could further enhance the therapeutic effect.

In one aspect, there is provided in the present application an antibody or an antigen-binding fragment thereof capable of specifically binding to CLDN18.2. In particular, the antibody comprises a heavy chain and a light chain, wherein (i) the heavy chain comprises three CDR regions, and the amino acid sequence of at least one of the CDR regions has the amino acid sequence as set forth in SEQ ID NO: 1, 2 or 3 or a sequence having at least 80% (preferably 85%, 90%, 95%, 98% or 99%) sequence identity to SEQ ID NO: 1, 2 or 3; and/or (ii) the light chain comprises three CDR regions, and the amino acid sequence of at least one of the CDR regions has the amino acid sequence as set forth in SEQ ID NO: 4, 5 or 6 or a sequence having at least 80% (preferably 85%, 90%, 95%, 98% or 99%) sequence identity to SEQ ID NO: 4, 5 or 6.

In some particular embodiments, the antibody comprises a heavy chain and a light chain, wherein (i) the heavy chain comprises three CDR regions having the amino acid sequences as set forth in SEQ ID NOS: 1, 2, and 3, respectively; and/or (ii) the light chain comprises three CDR regions having the amino acid sequences as set forth in SEQ ID NOS: 4, 5 and 6, respectively.

In certain embodiments, an antibody or an antigen-binding fragment thereof of the present application is in an isolated form.

In certain embodiments, the heavy chain comprises a heavy chain variable region having the amino acid sequence as set forth in SEQ ID NO:7, and/or the light chain comprises a light chain variable region having the amino acid sequence as set forth in SEQ ID NO:8.

In certain embodiments, the heavy chain comprises the amino acid sequence as set forth in SEQ ID NO:9, and/or the light chain comprises the amino acid sequence as set forth in SEQ ID NO:10.

In certain embodiments, the antibodies of the present application are monoclonal antibodies.

In certain embodiments, the antibodies of the present application are bispecific antibodies. For example, one arm of a bispecific antibody may be an antigen-binding fragment (e.g., Fab or scfv) of an anti-CLDN18.2 antibody described herein, and the other arm may be an antigen-binding fragment (e.g., Fab or scfv) that targets another antigen (e.g., other antigen targets useful for ADC construction) or another CLDN18.2 epitope (e.g., different from the CLDN18.2 epitope to which the anti-CLDN18.2 antibody described herein binds).

In certain embodiments, the antibodies of the present application are humanized antibodies, including semi-humanized antibodies and fully humanized antibodies.

In certain embodiments, an antibody or an antigen-binding fragment thereof of the present application has ADCC activity.

In certain embodiments, an antibody or an antigen-binding fragment thereof of the present application has CDC activity.

In certain embodiments, an antibody or antigen-binding fragment thereof of the present application specifically binds to CLDN18.2 while substantially not binding to CLDN18.1.

In certain embodiments, the antibody comprises a heavy chain constant region of IgG1 subtype, IgG2 subtype, or IgG4 subtype.

In certain embodiments, the heavy chain constant region of an antibody can be of human IgG1 subtype, human IgG2 subtype, human IgG4 subtype, murine IgG1 subtype, or murine IgG2a subtype.

In certain embodiments, the heavy chain constant region is of IgG1 subtype, i.e., an IgG1 type antibody.

In certain embodiments, the antibody comprises a light chain constant region of κ subtype or λ subtype.

In certain embodiments, the light chain constant region of an antibody can be of human κ subtype, human λ subtype, murine κ subtype, or murine λ subtype.

In certain embodiments, the antibody of the present application is an IgG1κ antibody.

In certain embodiments, the antibody or antigen-binding fragment thereof of the present application is useful in the treatment or prevention of cancer, wherein the cancer overexpresses CLDN18.2.

In one embodiment, the antibody having the ability to bind to CLDN18.2 binds to a natural epitope of CLDN18.2 present on the surface of a living cell. In one embodiment, the antibody having the ability to bind to CLDN18.2 binds to the extracellular domain of CLDN18.2. In one embodiment, the antibody having the ability to bind to CLDN18.2 binds to the first extracellular region of CLDN18.2.

In another aspect, there is provided in the present application an isolated polynucleotide encoding the antibody of the present application.

In yet another aspect, there is provided in the present application a combination of isolated polynucleotides comprising a polynucleotide encoding a light chain of an antibody or an antigen-binding fragment thereof of the present application and a polynucleotide encoding a heavy chain of an antibody or an antigen-binding fragment thereof of the present application.

In another aspect, there is provided in the present application an expression vector comprising a polynucleotide as described herein or a combination of polynucleotides as described herein operably linked to a regulatory sequence that allows expression of a polypeptide encoded by the polynucleotide(s) in a host cell or cell-free expression system.

In some embodiments of the present application, the host cell may be a prokaryotic host cell, a eukaryotic host cell, or a phage. The prokaryotic host cell may be *Escherichia coli, Bacillus subtilis, Streptomyces* or *Proteus mirabilis*. The eukaryotic host cell may be fungi such as *Pichia pastoris, Saccharomyces cerevisiae, Schizosaccharomyces cerevisiae*, or *Trichoderma*, insect cells such as *Spodoptera frugiperda*, or plant cells such as tobacco, mammal cells, such as BHK cells, CHO cells, COS cells, or myeloma cells. In some embodiments, the host cells described herein are preferably mammal cells, more preferably BHK cells, CHO cells, NSO cells, or COS cells.

In another aspect, there is provided in the present application an antibody-drug conjugate comprising an anti- CLDN18.2 antibody or an antigen-binding fragment thereof of the present application conjugated with one or more drug molecules. The embodiments and features of the anti-CLDN18.2 antibody or antigen-binding fragment thereof of the present application are described above.

Since CLDN18.2 is primarily a molecular target for cancer/tumor cells, in some embodiments, the drug molecule is an anticancer drug. However, it will be appreciated by those skilled in the art that when CLDN18.2 is the target in diseases other than cancer/tumor, the drug molecule may be selected according to the disease of interest.

Anticancer drugs include, but are not limited to, a cytotoxic drug, an immunopotentiator, or a radioisotope.

In some embodiments, a cytotoxic drug includes a tubulin inhibitor (e.g., an alkaloid), a DNA topoisomerase inhibitor, a DNA damaging agent, an antimetabolite, or an antitumor antibiotic.

In some embodiments, a tubulin inhibitor includes, but is not limited to, an auristatin derivative (e.g., MMAE (Monomethyl auristatin E), MMAF (Monomethyl auristatin F)) or a maytansine alkaloid derivative (e.g., DM1, DM4, Ansamitocin, Mertansine, or dolastatin or a derivative thereof).

In some embodiments, a DNA topoisomerase inhibitor is a camptothecin analog or a DNA topoisomerase I inhibitor or a derivative thereof, such as, DXD, SN38, irinotecan, irinotecan hydrochloride, camptothecin, 9-aminocamptothecin, 9-nitrocamptothecin, 10-hydroxycamptothecin, 9-chloro-10-hydroxycamptothecin, 22-hydroxyacuminatine, topotecan, lertonotecan, belotecan, ixitecan, homosilatecan, 6,8-dibromo-2-methyl-3-[2-(D-xylopyranosylamino)phenyl]-4(3H)-quinazolinone, 2-cyano-3-(3,4-dihydroxyphenyl)-N-(phenylmethyl)-(2E)-2-acrylamide, 2-cyano-3-(3,4-dihydroxyphenyl)-N-(3-hydroxyphenylpropyl)-(E)-2-acrylamide, 12-β-D-glucopyranosyl-12,13-dihydro-2,10-dihydroxy-6-[[2-hydroxy-1-(hydroxymethyl)ethyl]amino]-5H-indoleindolo[2,3-a]pyrrolo[3,4-c]carbazole-5,7(6H)-dione, N-[2-(dimethylamino)ethyl]-4-acridine formamide dihydrochloride, N-[2-(dimethylamino)ethyl]-4-acridinecarboxamide.

In some embodiments, a DNA damaging agent includes, but is not limited to, calicheamicin, duocarmycin, or pyrrolobenzodiazepine PBD (an anthramycin derivative).

In some embodiments, an immunoenhancers includes, but is not limited to, levamisole, pidomod, imiquimod, isoinosine, polyinosinic:polycytidylic acid, or polyinosinic:polyuridinic acid.

In some embodiments, an antimetabolite includes, but is not limited to, methotrexate, 6-mercaptopurine, or 5-fluorouracil.

In some embodiments, anti-tumor antibiotics include, but are not limited to, polypeptide antibiotics (e.g., actinomycin D or bleomycin) or anthraquinones (e.g., doxorubicin or mitoxantrone hydrochloride).

In some embodiments, a radioisotope includes, but is not limited to, $^{211}At$, $^{131}I$, $^{125}I$, $^{90}Y$, $^{186}Re$, $^{188}Re$, $^{153}Sm$, $^{212}Bi$, $^{32}P$, $^{60}Co$, or $^{177}Lu$.

In some embodiments, an antibody having the ability to bind to CLDN18.2 is covalently linked to a drug moiety via a linker. In some embodiments, the linker is a cleavable linker. In some embodiments, the linker can be cleaved under intracellular conditions. In one embodiment, the linker can be cleaved at a pH of less than 5.5. In some embodiments, the linker can be cleaved by an intracellular protease. In some embodiments, the linker is a cathepsin cleavable linker. In some embodiments, the linker comprises a dipeptide. In some embodiments, the dipeptide is valine (Val)-citrulline (Cit). In some embodiments, the antibody is attached to the linker through a thiol group of a cysteine of the antibody. In one embodiment, the antibody is attached to the linker through an amino group of the antibody, in particular an amino group of a glutamine residue.

Non-limiting examples of linkers include mc-Val-Cit-pAB, mc-Val-Cit-pABC, mc-Val-Cit, $NH_2$-$(PEG)_m$-Val-Cit, $NH_2$-$(PEG)_m$-Val-Cit-pAB, where m is an integer from 1 to 8.

In certain embodiments, the antibody-drug conjugates described herein have the general formula Ab-$(L\text{-}U)_n$, wherein Ab represents an anti-CLDN18.2 antibody of the present application, L is a linker (e.g., $NH_2$-$(PEG)_m$-Val-Cit, $NH_2$-$(PEG)_m$-Val-Cit-pAB, $NH_2$-$(PEG)_m$-Val-Cit-pABC, mc-Val-Cit-pAB, or Val-Cit, wherein m represents the number of PEG, which may be an integer from 1 to 8), and U is a drug (e.g., DM1, DM4, MMAE, MMAF, DXD and SN38), and n represents a drug antibody ratio (DAR). The DAR value may be an average value, and may be any value (not limited to an integer, but may also be a decimal number) from 1 to 8, preferably an integer from 1 to 8, more preferably 2, 4, 6, 8, even more preferably 2.

In another aspect, there is provided in the present application a pharmaceutical formulation (e.g., a pharmaceutical composition) comprising an antibody-drug conjugate of the present application, and a pharmaceutically acceptable diluent, carrier, or excipient.

In another aspect, there is provided in the present application a medical preparation comprising an antibody-drug conjugate of the present application. In some embodiments, the medical preparation is in the form of a kit comprising a container containing the antibody-drug conjugate of the present application. In one embodiment, the medical preparation further comprises printed instructions for using the preparation in a method of treating or preventing cancer, in particular cancer expressing CLDN18.2.

The antibody-drug conjugates provided herein are effective in treating and/or preventing cancer associated with cells expressing CLDN18.2 (CLDN18.2 positive). By way of non-limiting example, the cancer may be gastric cancer, esophageal cancer, pancreatic cancer, lung cancer (e.g., non-small cell lung cancer (NSCLC)), ovarian cancer, colon cancer, liver cancer, head and neck cancer, or gallbladder cancer, and metastases of the aforementioned cancer, in particular gastric cancer metastases, peritoneal metastases, and lymph node metastases. Cancer suitable for treatment with the antibody-drug conjugate provided herein may be adenocarcinomas of stomach, esophagus, pancreatic duct, bile duct, lung and ovary. The antibody-drug conjugates provided herein are particularly suitable for the treatment of gastric cancer and pancreatic cancer.

Thus, the present application further provides inventions related to the above therapeutic use.

In one aspect, there is provided in the present application use of an antibody-conjugate described above in the manufacture of a medicament for the treatment or prevention of cancer.

In another aspect, there is provided in the present application a method of treating cancer in a subject, comprising administering to the subject suffering from the cancer a therapeutically effective amount of an antibody-conjugate or a pharmaceutical formulation or pharmaceutical composition comprising the conjugate as described above.

In another aspect, there is provided in the present application use of an antibody-conjugate as described above and an anti-proliferative agent in the manufacture of a medicament for the treatment of a tumor, such as cancer as described above.

In another aspect, there is provided in the present application a pharmaceutical composition comprising an antibody-conjugate described above and an anti-proliferative agent.

In another aspect, there is provided in the present application a method of treating a tumor in a subject, comprising administering to the subject suffering from the tumor a therapeutically effective amount of an antibody-conjugate or a pharmaceutical formulation or pharmaceutical composition comprising the antibody-conjugate as described above and an anti-proliferative agent.

In particular embodiments, an anti-proliferative agent includes, but is not limited to, paclitaxel, doxorubicin, docetaxel, cisplatin, carboplatin, or isoplatin. In certain embodiments, the anti-proliferative agent may also be a different antibody, antibody-drug conjugate, or fusion protein.

EXAMPLES

The following examples are provided for purposes of illustration only and are not intended to limit the scope of the present application.

Experimental Equipment and Materials

| Instrument and equipment | Manufacturer | Model |
|---|---|---|
| Flow cytometry | Thermo Fisher | Attune ® NxT |
| Carbon dioxide incubator | Thermo Fisher | 3111 type |
| Biosafety cabinet | Thermo Fisher | 1300 Series A2 6 inches |
| Table type high-speed freezing centrifugal machine | Thermo Fisher | SORVALL Stratos |
| Inverted microscope | Olympus | CKX31 inverted microscope |
| Carbon dioxide incubator | Thermo Fisher | 3111 type |
| Biosafety cabinet | Thermo Fisher | 1300 Series A2 6 inches |
| Table type high-speed freezing centrifugal machine | Thermo Fisher | SORVALL Stratos |
| Inverted microscope | Olympus | CKX31 inverted microscope |
| Laser confocal microscope | Olympus | FV3000 |
| Microplate reader | Tecan | M200 |
| 96-well transparent flat bottom cell culture plate | Corning | 3599 |
| 96-well black flat bottom cell culture plate | Corning | 3603 |
| Sample dilution tank | BIOFIL | LTT012100, 100 ml |
| Zenon ™ pHrodo ™ iFL IgG Labeling Reagents | Invitrogen | Z25611 |
| Pipette | Eppendorf | Research Plus |
| 96-well V-type culture plate | Corning | 3897 |
| 50 mL centrifuge tube | Corning | 430828 |
| 15 mL centrifuge tube | Corning | 430790 |
| T75 cell culture flasks | Corning | 430641 |
| T25 cell culture flasks | Corning | 430639 |
| DPBS | BBI | E607009-0500 |
| 1 × focusing liquid | Life technologies | A24904 |
| 1 × stop fluid | Life technologies | A24975 |
| Washing liquid | Life technologies | A24974 |
| Fetal bovine serum | Gibco | 10099-141C |
| DMEM medium | Hyclone | SH30243.01 |
| RPMI medium | HyClone | SH30809.01 |
| Resazurin sodium salt | Sigma | 199303-25G |
| Anti-Anti (100×) | Gibco | 15240-062 |
| DMEM/F-12 medium | Gibco | C11330500BT |
| 0.25% Trypsin -EDTA | Gibco | 25200-072 |
| Puromycin | Thermo | A1113802 |
| G418 | Sigma | a1720-5g |
| Goat anti-human IgG (H + L) cross-adsorbed secondary antibody, Alexa Fluor 488 | Invitrogen | A11013 |

Cell Lines Used in Experiments

| Name | Manufacturer | Culture conditions |
|---|---|---|
| HEK293-huCLDN18.2 | self-made | DMEM complete medium +200 μg/mL G418 |
| HEK293-Mouse CLDN18.2 | Kangyuan Baochuang | DMEM complete medium +0.5 μg/ml puromycin |
| Cynomolgus CLDN18.2 CHO-K1 | Gemini Bio | DMEM/F-12 complete medium ATCC Number: CCL-61, Lot No.: 59965043 |
| HEK293-CLDN18.1 | self-made | DMEM complete medium +200 μg/mL G418 |
| HEK 293 | Nanjing Kebai | DMEM complete medium |
| KATOIII | Nanjing Kebai | RPMI complete medium |
| NCI-N87-CLDN18.2 | Kangyuan Baochuang | RPMI complete medium +0.5 μg/ml puromycin |
| NCI-H460-CLDN18.2 | self-made | RPMI complete medium +1 μg/ml puromycin |
| NUG4-CLDN18.2 | self-made | RPMI complete medium +500 μg/ml G418 |
| PATU8988S | Nanjing Kebai | DMEM complete medium |
| BxPC-3-CLDN18.2 | Kangyuan Baochuang | DMEM complete medium +1 μg/ml puromycin |

Example 1: Preparation of Fully Human Anti-CLDN18.2 Monoclonal Antibody

The anti-CLDN18.2 antibodies used in the present application were produced by immunization of human Ig transgenic mice. Transgenic mice were immunized with CHO cells or 3T3 cells transfected with human CLDN18.2. Immunogens were injected intraperitoneally (IP), subcutaneously (SC), or into the foot pad (fp) or the tail of the mice. The immune response was tested by periodically detecting the titer of anti-CLDN18.2 in plasma. Mice with sufficient anti-CLDN18.2 titer in plasma were used for hybridoma fusion. Immunopotentiation was performed by injecting the immunogens into the peritoneum, foot pads, or the tail vein of the mice prior to the final removal of the spleen and lymph nodes from the mice.

Sera from immunized mice were screened by fluorescence activated cell sorting (FACS). Mice producing antibodies binding to CLDN18.2 were selected. Cell lines expressing CLDN18.2 (CHO or 3T3) were first incubated with gradient diluents of sera from immunized mice. Then, specific antibody binding was detected with PE fluorescently labeled anti-mouse IgG Ab on a fluorescence activated cell sorting device (iQue plus, Sartorius). In addition, sera from mice were confirmed by imaging testing. CHO cells (or 3T3 cells) expressing CLDN18.2 were incubated with diluents of sera from immunized mice. Then, the cells were washed, fixed with formaldehyde, and washed again. Specific antibody binding was detected with Alexa488 fluorescently labeled goat anti-mouse antibody, with scanning and analysis on a cell imager (Cytation 5, Biotek). After identification of the mice producing antibodies that bind to CLDN18.2, spleen and lymph nodes were removed from the immunized mice. Lymphocytes were isolated, fused to mouse myeloma cells Sp2/0 (ATCC, CRL 1581) by electrofusion. The resulting hybridomas were screened for specific anti-CLDN18.2 antibodies. Cells were plated in flat bottom 96-well tissue culture plates, incubated in a selection medium (HAT medium) for 2 weeks, and then moved to a hybridoma medium for further culture. Approximately 10 to 14 days after cell plating, supernatants for hybridoma culture from individual wells were subjected to anti-CLDN18.2 specific binding imaging by the aforementioned cellular imaging screening method. The related hybridoma cells were selected from hybridomas produced by a group of three mice upon immunization. Hybridoma cells generated by electrofusion after immunization of mice were plated in flat bottom 96-well tissue culture plates, each well containing one or several hybridoma cells. The supernatant of hybridoma culture from a single well was tested by cellular imaging methods, and the supernatant from the clone secreting positive antibodies specifically bound to CHO cells transfected with CLDN18.2 but not to CHO cells or CHO cells transfected with CLDN18.1. Hybridomas secreting positive antibodies were transferred to 24-well plates and re-screened for confirmation. Confirmed positive antibody-producing hybridomas were sorted by using a single cell sorter. Each positive hybridoma was sorted for 96 subclones which were re-screened for confirmation. The positive subclones which produced preliminary candidate molecules were cultured in vitro for sequencing. Small amounts of antibodies produced by the positive subclones were used for purification, characterization and validation. The obtained antibody SYJS001 has the following relevant sequences.

TABLE 1

| Antibody region/taxonomy | IMGT CDR definition: |
|---|---|
| FR-H1 | EVQLSESGGALVQPGESLRLSCAAS (SEQ ID NO: 11) |
| CDR-H1 | GFTFSSYA (SEQ ID NO: 1) |
| FR-H2 | MTWVRQAPGKGLEWVSS (SEQ ID NO: 12) |
| CDR-H2 | LSGSGRST (SEQ ID NO: 2) |
| FR-H3 | YYAASIKGRFTISRDNSKNTLYLQMSSLRAEDTAIYYC (SEQ ID NO: 13) |
| CDR-H3 | AKSLSYYHYYFDY (SEQ ID NO: 3) |
| FR-H4 | WGQGTLVTVSS (SEQ ID NO: 14) |
| FR-L1 | DIQLTQSPSFLSASVGDRVPITCRAS (SEQ ID NO: 15) |
| CDR-L1 | QDISNY (SEQ ID NO: 4) |
| FR-L2 | LAWYQQKPGKAPKLLIY (SEQ ID NO: 16) |
| CDR-L2 | SAS (SEQ ID NO: 5) |
| FR-L3 | TLQSGVPSRFSGSGSGTEFTLTISSLQPEDFASYHC (SEQ ID NO: 17) |
| CDR-L3 | QQVKTYPLT (SEQ ID NO: 6) |
| FR-L4 | FGGGTKVEIK (SEQ ID NO: 18) |

(Heavy Chain Variable Region)

SEQ ID NO: 7

```
EVQLSESGGALVQPGESLRLSCAASGFTFSSYAMTWVRQAPGKGLEWVS
SLSGSGRSTYYAASIKGRFTISRDNSKNTLYLQMSSLRAEDTAIYYCAK
SLSYYHYYFDYWGQGTLVTVSS
```

(Light Chain Variable Region)

SEQ ID NO: 8

```
DIQLTQSPSFLSASVGDRVPITCRASQDISNYLAWYQQKPGKAPKLLIY
SASTLQSGVPSRFSGSGSGTEFTLTISSLQPEDFASYHCQQVKTYPLTF
GGGTKVEIK
```

(Heavy Chain)

SEQ ID NO: 9

```
EVQLSESGGALVQPGESLRLSCAASGFTFSSYAMTWVRQAPGKGLEWVS
SLSGSGRSTYYAASIKGRFTISRDNSKNTLYLQMSSLRAEDTAIYYCAK
SLSYYHYYFDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK
```

(Light Chain)

SEQ ID NO: 10

```
DIQLTQSPSFLSASVGDRVPITCRASQDISNYLAWYQQKPGKAPKLLIY
```

-continued

```
SASTLQSGVPSRFSGSGSGTEFTLTISSLQPEDFASYHCQQVKTYPLTF

GGGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Example 2: Vector Construction and Antibody Expression 2.1 Vector Design

Figure 3:
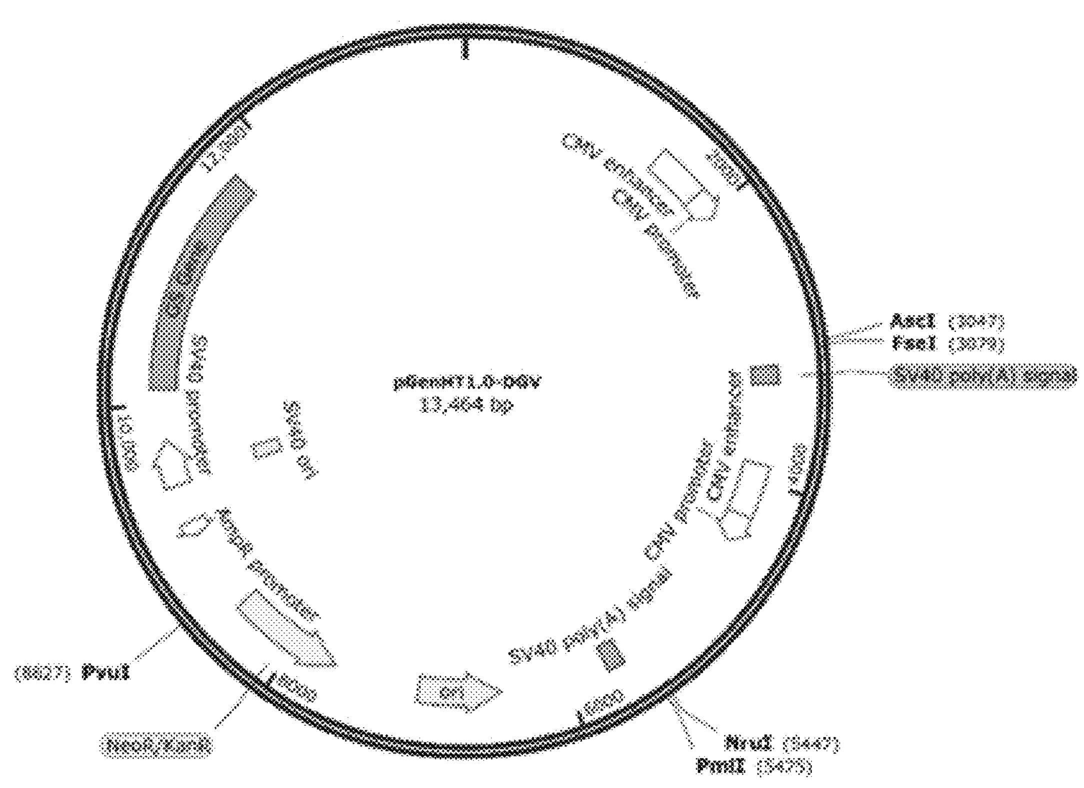
FIG. 3 shows the plasmid map of pGenHT1.0-DGV.

The plasmid vector pGenHT1.0-DGV used for expression of SYJS001 monoclonal antibody was provided by Nanjing GenScript Biotechnology Co., Ltd. ("GenScript"). The vector map is shown in FIG. 3 and the information about key elements is shown in Table 2:

TABLE 2

Information of Key Element in Vector PGenHT1.0-DGV

| Element | Name | Function |
|---|---|---|
| CMV promoter | cytomegalovirus promoter | Driving foreign gene transcription |
| NeoR/KanR | neomycin resistance and kanamycin resistance genes | Screening host cells and *Escherichia coli* positive clones |
| GS gene | glutamine synthetase gene | expressing glutamine synthetase |

In this study, the heavy and light chain DNA sequences of SYJS001 and the expression vector pGenHT1.0-DGV were synthesized by GenScript.

Design and Synthesis of Heavy Chain:

The synthetic heavy chain was designated SYJS001-HC. An NruI endonuclease site was introduced into the 5' terminus, a PmLI endonuclease site was introduced into the 3' terminus, a Kozak sequence is introduced after the NruI endonuclease site in the 5' terminus, and a signal peptide sequence (19 amino acids, MGWSCIILFLVATATGVHS (SEQ ID NO:19)) was introduced. The expression frame of the heavy chain was designed as:

NruI-Kozak sequence-signal peptide-SYJS001-HC-stop codon-PmLI

Figure 4:
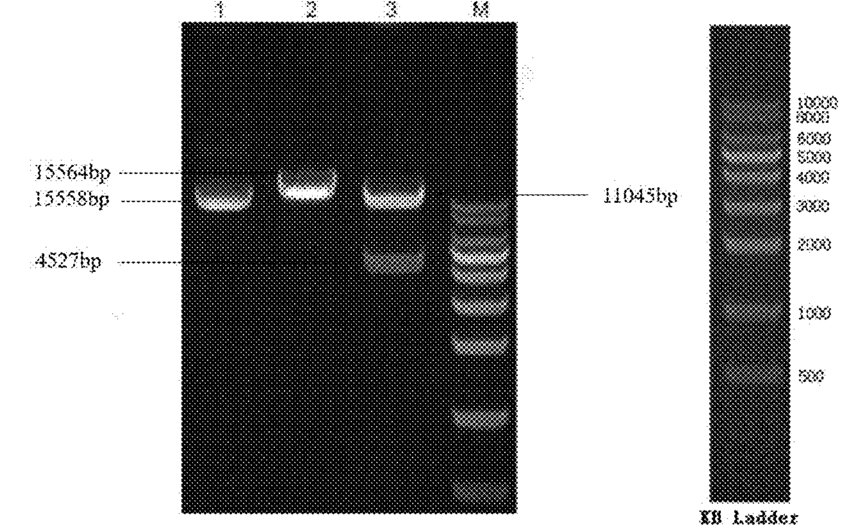
FIG. 4 shows a double enzyme digestion map of the SYJS001 in pGenHT1.0-DGV plasmid. Lane M denotes the KB Ladder; Lane 1 denotes the superspiral state; Lane 2 denotes a linearized plasmid formed by digestion with PvuI; Lane 3 denotes the heavy chain, light chain and remaining fragments formed by digestion with AscI/PmLI.
Figure 5:
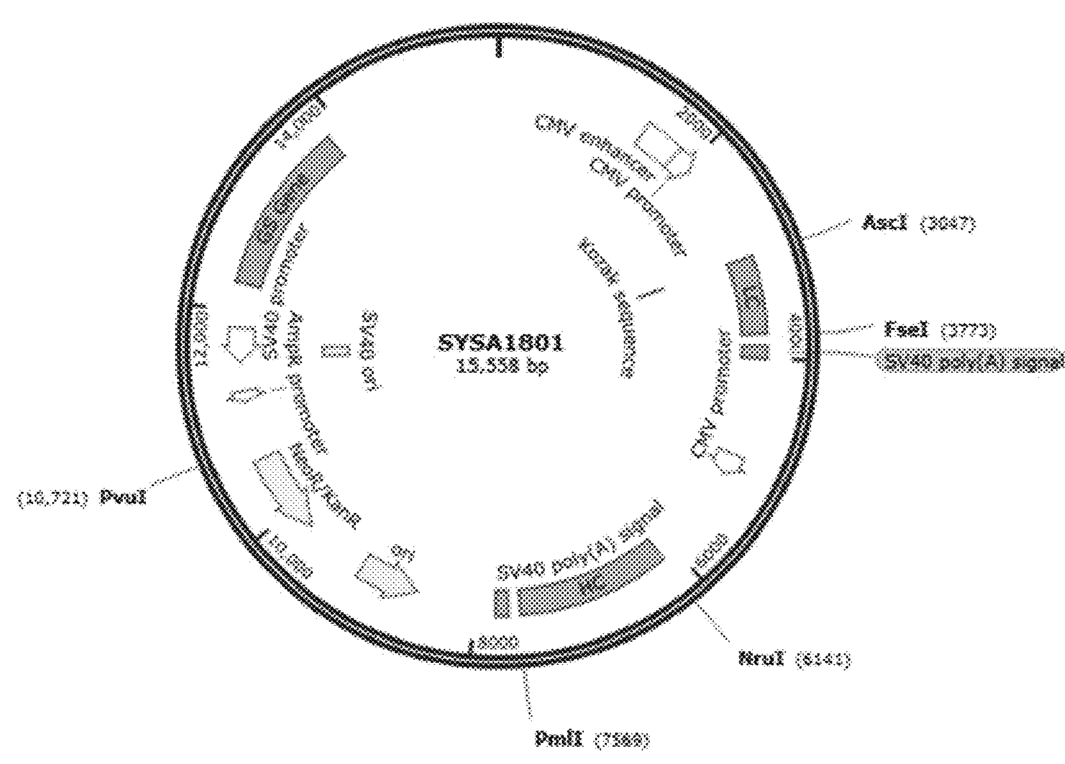
FIG. 5 shows a schematic diagram of the SYJS001 in pGenHT1.0-DGV plasmid.

Design and Synthesis of Light Chain:

The synthetic light chain was designated SYJS001-LC. During synthesis, an AscI endonuclease site was introduced into the 5' terminus, an FseI endonuclease site was introduced into the 3' terminus, a Kozak sequence is introduced after the AscI endonuclease site in the 5' terminus, and a signal peptide sequence (19 amino acids, MGWSCIILFLVATATGVHS (SEQ ID NO:19)) was introduced. The expression frame of the light chain was designed as:

AscI-Kozak sequence-signal peptide-SYJS001-LC-stop codon-FseI 2.2 Construction of Recombinant Vector The SYJS001-HC insertion site is the downstream polyclonal NruI/PmLI site of the pGenHT1.0-DGV vector and the SYJS001-LC insertion site is the upstream polyclonal AscI/FseI site. The promoters of both multiple cloning sites were CMV. The heavy and light chains were constructed on the same empty vector. The PCR amplification product SYJS001-HC and the plasmid vector pGenHT1.0-DGV were subjected to NruI/PmLI double enzyme digestion and ligation transformation. Positive clones were screened by means of Kan+ resistance marker to obtain the correct recombinant heavy chain expression vector, which was designated SYJS001-HC in pGenHT1.0-DGV. Next, light chain SYJS001-LC and SYJS001-HC in pGenHT1.0-DGV were subjected to AscI/FseI double enzyme digestion, ligation transformation, and clone screening. Positive clones were digested with AscI/PmLI (see FIG. 4) and sequenced to obtain a correct recombinant heavy and light chain expression vector, which was designated SYJS001 in pGenHT1.0-DGV with the structure shown in FIG. 5. SYJS001 in pGenHT1.0-DGV was subjected to double enzyme digestion for confirmation. The sequence of the target region was 4527 bp in length. The recombinant plasmid obtained was electroporated into host cell CHO K1 to obtain a cell strain with stable and high expression of SYJS001 antibody.

2.3 Expression and Purification of Antibodies

The cell strain with stable and high expression of SYJS001 antibody was incubated in serum-free CD Ford CHO in flasks. The culture supernatants were collected after a certain period of time. HiTrap Mab Select SuRe 1 ml columns were equilibrated with a PBS solution (pH=7.4, 10 times column volume) (GE Healthcare Life Sciences, Cat. No. 11-0034-93) at a flow rate of 0.5 ml/min. The culture supernatant was loaded for filtration through a 0.45 μm membrane at a flow rate of 0.5 ml/min. The columns were washed with the PBS solution (pH=7.4, 5-10 times column volume) at a flow rate of 0.5 ml/min. Elution was done with a 100 mM citric acid buffer (pH3.6) at a flow rate of 0.5 ml/min, and the eluted fractions were collected to obtain SYJS001 antibody with a purity of >95%.

Example 3: Preparation of SYJS001 ADC

Figure 1:
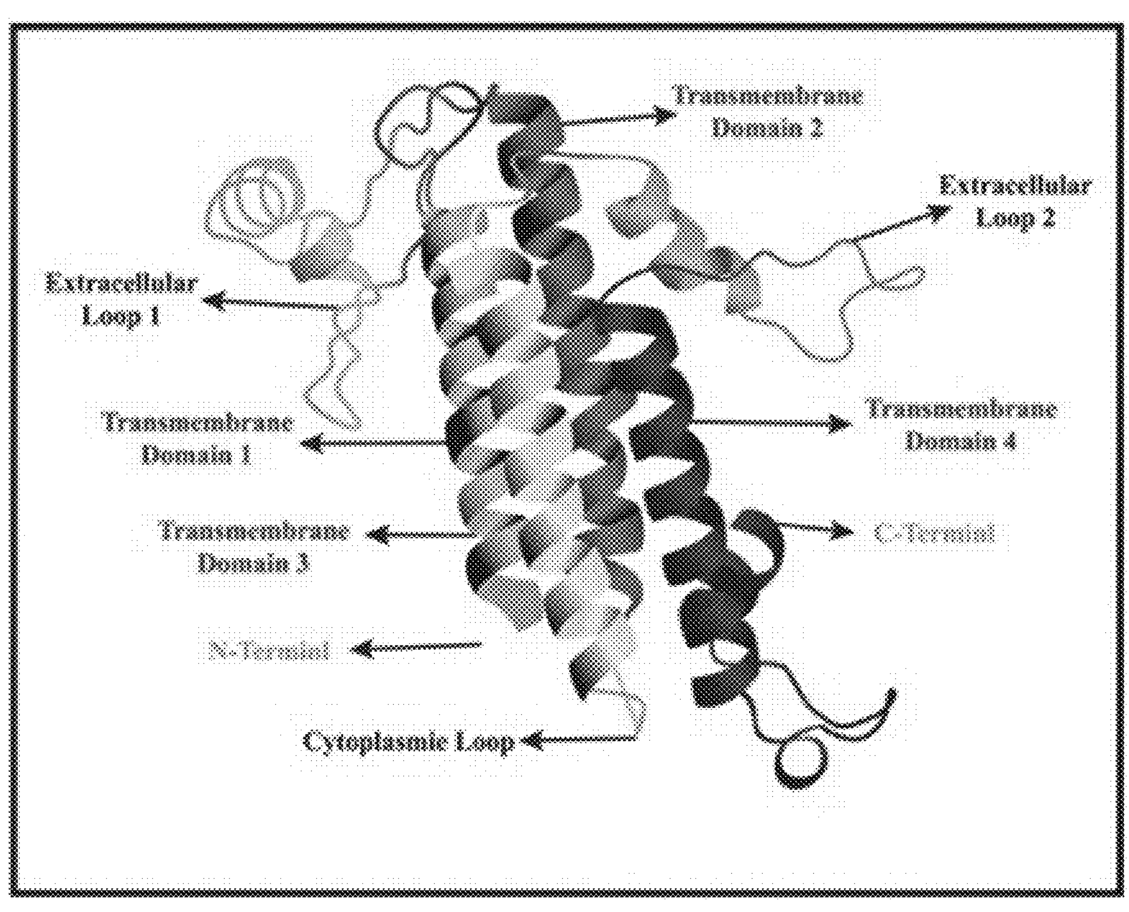
FIG. 1 shows a schematic diagram of the structure of Claudin.
Figure 2:
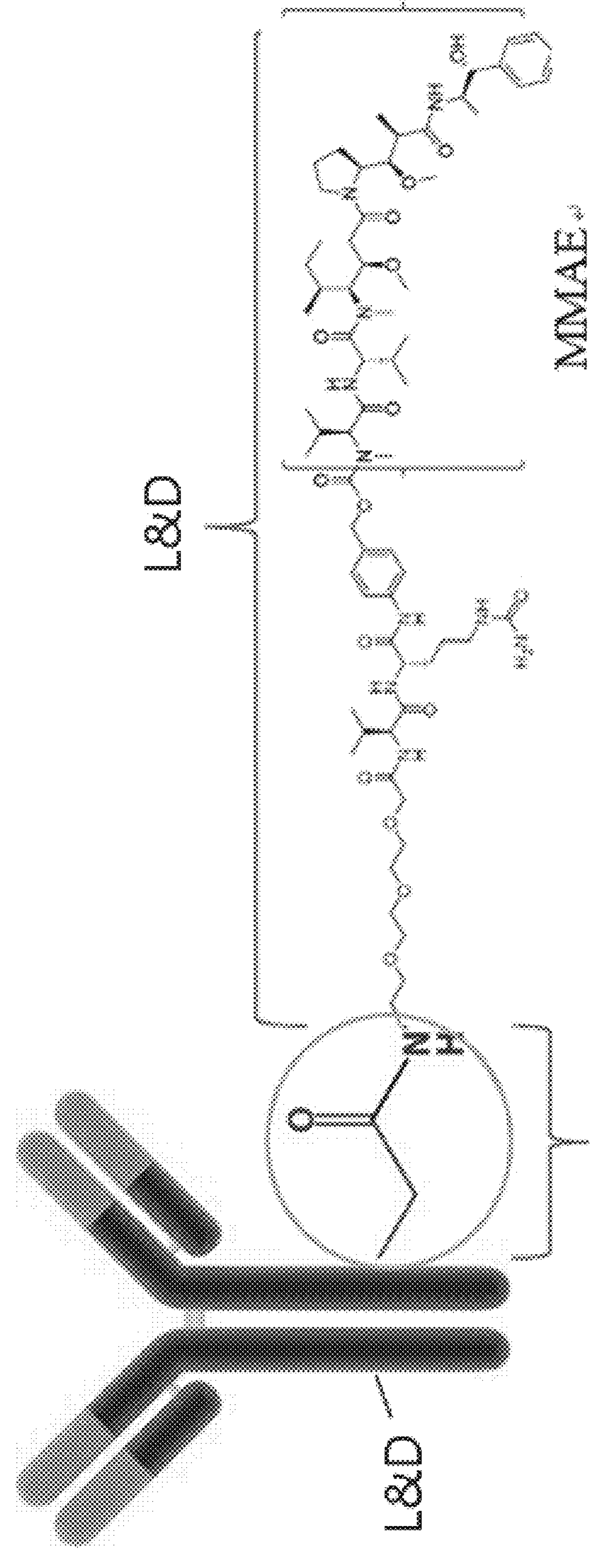
FIG. 2 shows a schematic diagram of the structure of SYJS001 ADC, in which L&D denotes the linker (Linker, "L") plus the drug molecule (Drug, "D"), the L&D on the right shows the complete structure, and the circle-labeled part denotes that the linker in L&D is attached to the antibody via amide bonds. SYJS001 ADC demonstrated in the present application is a site-specific antibody-drug conjugate, each molecule consisting of a fully human anti-CLDN18.2 monoclonal antibody (SYJS001 mAb) coupled to an MMAE derivative molecule via a linker ($NH_2$-$PEG_3$-Val-Cit) at amino acid Q298 (i.e., Kabat number Q295) of each heavy chain. The antibody and the linker are connected via a stable amide bond (isopeptide bond). The average drug to antibody ratio (DAR) is 2.0, and a relative molecular weight is 150 KD.

A certain amount of L&D (structure shown in FIG. 2), reaction buffer, SYJS001 antibody, mTGase (transglutaminase) and $H_2O$ were transferred to an elastic ethylene-vinyl acetate disposable reaction bag by peristaltic pump in an appropriate order. The reaction bag was sealed, and the reactants were mixed and incubated at 30° C. for a reaction period of 24-144 h. The coupling rate was determined by the C4-HPLC assay every 24 hours during the reaction. When the coupling rate was >=95%, the reaction was terminated and the reactant was immediately purified.

The transglutaminase as used had the following amino acid sequence:

```
                                             (SEQ ID NO: 20)
DSDERVTPPAEPLDRMPDPYRPSYGRAETIVNNYIRKWQQVYSHRDGRK

QQMTEEQREWLSYGCVGVTWVNSGQYPTNRLAFAFFDEDKYKNELKNGR

PRSGETRAEFEGRVAKDSFDEAKGFQRARDVASVMNKALENAHDEGAYL

DNLKKELANGNDALRNEDARSPFYSALRNTPSFKDRNGGNHDPSKMKAV

IYSKHFWSGQDRSGSSDKRKYGDPEAFRPDRGTGLVDMSRDRNIPRSPT

SPGESFVNFDYGWFGAQTEADADKTVWTHGNHYHAPNGSLGAMHVYESK

FRNWSDGYSDFDRGAYVVTFVPKSWNTAPDKVTQGWP
```

Example 4: Analysis and Characterization of SYJS001 ADC's Physicochemical Properties 1. Identification of SYJS001 ADC's Modification Rate Experimental Procedures:

1) Loading: 10 μl of supernatant from the reduced ADC reactant sample was taken and loaded onto a chromatographic column (waters xbridge C4, 3.5 μm, 4.6 mm*250 mm).

2) Elution: The mobile phase A was 0.1% TFA aqueous solution and the mobile phase B was 0.1% acetonitrile solution. The mobile phase A:B ratio was adjusted to 9:1, 7:3, 6.5:3.5, 6:4, 5.5:4.5, 5:5, 1:9 and 9:1 at 0, 5, 8, 15, 20, 22, 25 and 30 min for elution, respectively. The flow rate was controlled to be 0.8 ml/min and the detection wavelength was 280 nm.

Figure 6:
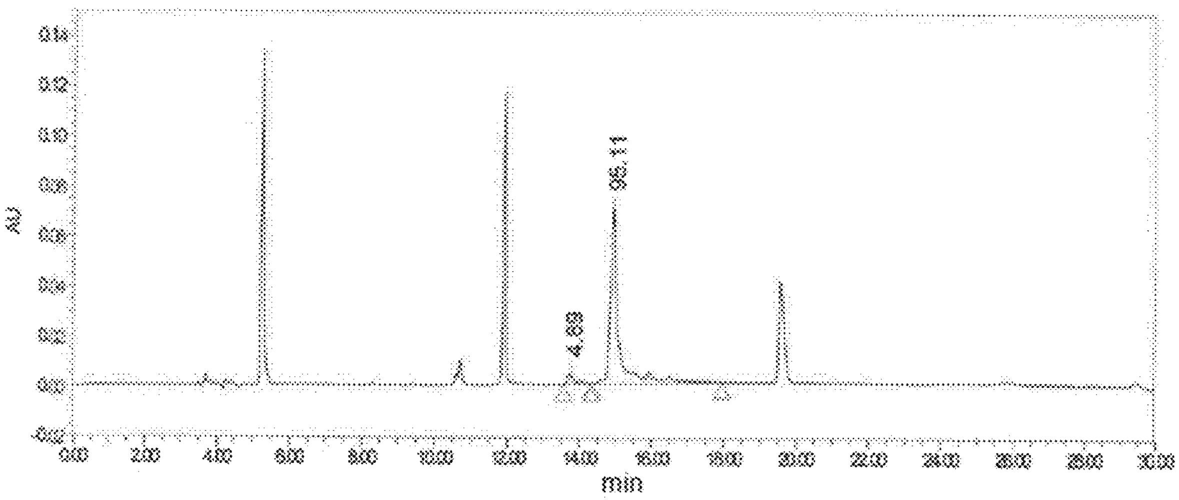
FIG. 6 shows an identification spectrum of SYJS001 ADC modification rate, where the peaks at 4.89 and 95.11 represent the anti-CLDN18.2 monoclonal antibody and the anti-CLDN18.2 monoclonal antibody-drug conjugate, respectively.

As shown by the experimental results in FIG. 6, the modification rate of SYJS001 ADC was 95.11%.

2. Measurement of SYJS001 ADC's DAR

Experimental Procedures:

1. Loading: 10 μg of SYJS001 ADC sample was loaded onto a chromatographic column (Agilient PLRP-S, 5 μm, 2.1 mm*50 mm).

Figure 7:
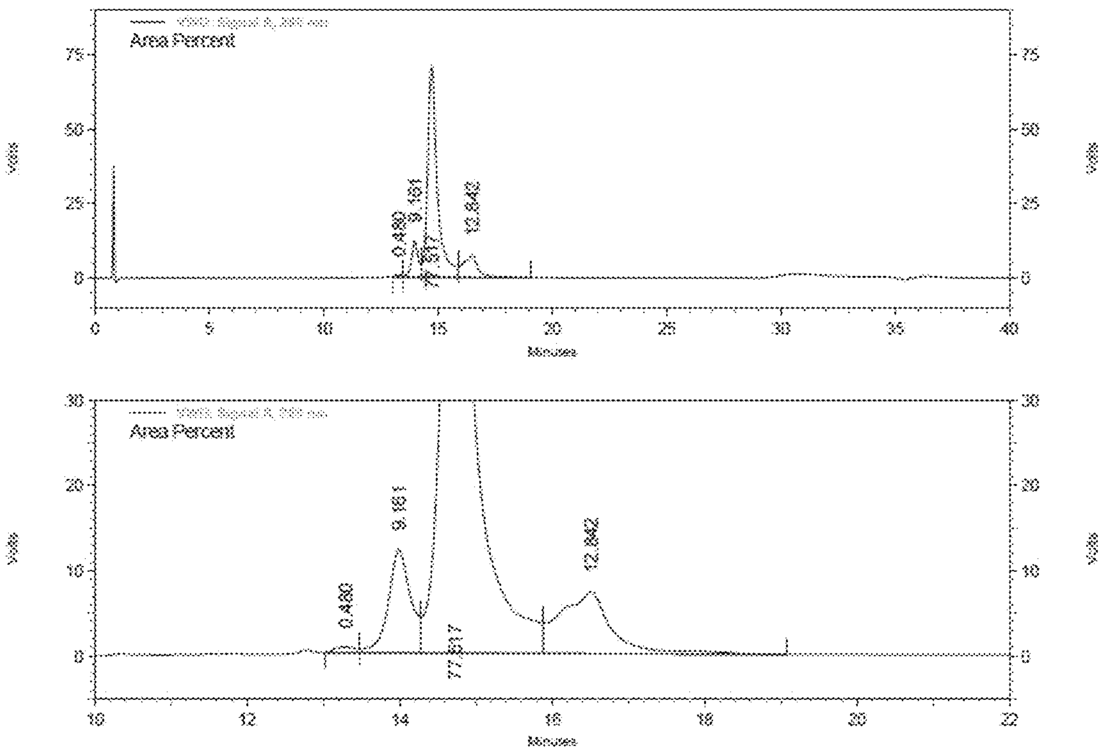
FIG. 7 shows an identification spectrum of SYJS001 ADC DAR distribution.

2. Elution: The mobile phase A was 0.1% TFA aqueous solution, and the mobile phase B was 0.1% acetonitrile solution. The mobile phase A:B ratio was adjusted to 7.3:2.1, 6.5:3.5, 5.7:4.3, 0.5:9.5 and 7.3:2.7 at 0, 8, 25, 26 and 31.5 min for elution, respectively. The flow rate was controlled to be 0.25 ml/min and the detection wavelength was 280 nm. As shown in FIG. 7, the average DAR was 2.

Example 5: Flow Cytometry Detection of Binding of SYJS001 ADC to CLDN18.2

The binding capacity of SYJS001 ADC to CLDN18.2 of different species was determined by flow cytometry.

Over-expressing cell lines (HEK293-human CLDN18.2, HEK293 mouse CLDN18.2, cynomolgus monkey CLDN18.2, CHO-K1) were incubated with SYJS001 ADC sample at different concentrations, and then incubated with IgG-binding secondary antibody (goat anti-human IgG (H+L) cross-adsorbed secondary antibody). Fluorescence signal values at different concentrations were measured by flow cytometry to analyze the binding capacity of the sample to CLDN18.2 of different species.

Figure 8:
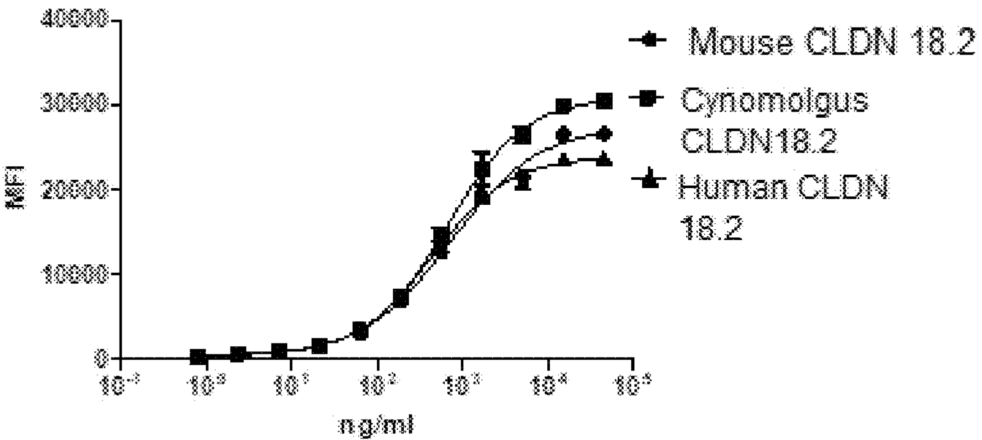
FIG. 8 shows the binding curves of SYJS001 ADC to cells expressing human, murine, and monkey CLDN18.2.

Experimental Procedures:

The SYJS001 ADC sample was diluted with a 3-fold gradient, starting at 45 μg/ml for a total of 11 gradients. 100 μl of sample at different concentrations were incubated with human, mouse and cynomolgus monkey CLDN18.2-expressing cells ($1\times10^6$ cells/ml, 100 μl/well) at 4° C. for 1.5 h. Unbound samples were removed by washing the cells, and goat anti-human IgG (H+L) cross-adsorbed secondary antibody (1:1000 dilution) was added for incubation for 1 h at 4° C. The data were analyzed using the GraphPad Prism 5 software. A regression model of the four-parameter equation was selected as the "S" curve, and the software automatically generated the half effective amount $ED_{50}$ (C value). As shown in FIG. 8 and Table 3, SYJS001 ADC had good affinity for human, mouse and cynomolgus monkey CLDN18.2.

TABLE 3

$ED_{50}$ Values of SYJS001 ADC in Binding to CLDN18.2 of Different Species

| Sample name | $ED_{50}$ (ng/ml) |
|---|---|
| HEK293-human CLDN18.2 | 439.1 |
| HEK293-mouse CLDN18.2 | 717.0 |
| Cynomolgus monkey CLDN18.2 CHO-K1 | 647.9 |

Example 6: Specific Binding of SYJS001 ADC to CLDN18.2

6.1. Specificity and Cross-Action of SYJS001 Monoclonal Antibody for CLDN18 Family Members CHOK1-CLDN18.2 and HEK293-CLDN18.1 cells were cultured with their corresponding complete mediums, respectively, and passaged every 2-3 days. When the cell fusion rate reached 90%, a cell suspension with the cell density adjusted to $2\text{-}3\times10^6$ cells/mL with the complete medium was plated into flow 96-well assay plates using a multi-channel pipette at 100 μL per well. The plates were centrifuged at 2500 rpm for 5 min and the supernatant were discarded. The plates were washed twice with 2% FBS/PBS. SYJS001 monoclonal antibody was diluted with 2% FBS/PBS buffer at a starting concentration of 6 μg/ml with a 3-fold gradient of 8 gradients. Two duplicates per concentration and a corresponding blank control were set. 100 μL of each antibody dilution was added per well, and the plates were incubated at 4° C. for 2 h. After the plates were washed three times with 2% FBS/PBS, 488 labelled goat anti-human IgG (1:5000 dilution) were added, and the plates were incubated at 4° C. for 1 h. After the plates were washed three times with 2% FBS/PBS, the plates were imported into corresponding fluorescence channels for reading.

6.2 Specific Binding of SYJS001 ADC to CLDN18.2

HEK293-CLDN18.2 cells were cultured with its corresponding complete medium and passaged every 2-3 days. When the cell fusion rate reached 90%, a cell suspension with the cell density adjusted to $2\text{-}3\times10^6$ cells/mL with the complete medium was plated into flow 96-well assay plates using a multi-channel pipette at 100 μL per well. The plates were centrifuged at 2500 rpm for 5 min and the supernatant were discarded. The plates were washed twice with 2% FB S/PB S. SYJS001 monoclonal antibody and SYJS001 ADC were diluted with 2% FBS/PBS buffer. The dilution of SYJS001 ADC was at a starting concentration of 15 μg/ml with a 3-fold gradient of 11 gradients. Two duplicates per concentration and a corresponding blank control were set. 100 μL of each ADC dilution was added per well, and the plates were incubated at 4° C. for 2 h. After the plates were washed three times with 2% FBS/PBS, 488 labelled goat anti-human IgG (1:1000 dilution) were added, and the plates were incubated at 4° C. for 1 h. After the plates were washed three times with 2% FBS/PBS, the plates were imported into corresponding fluorescence channels for reading.

Figure 9:
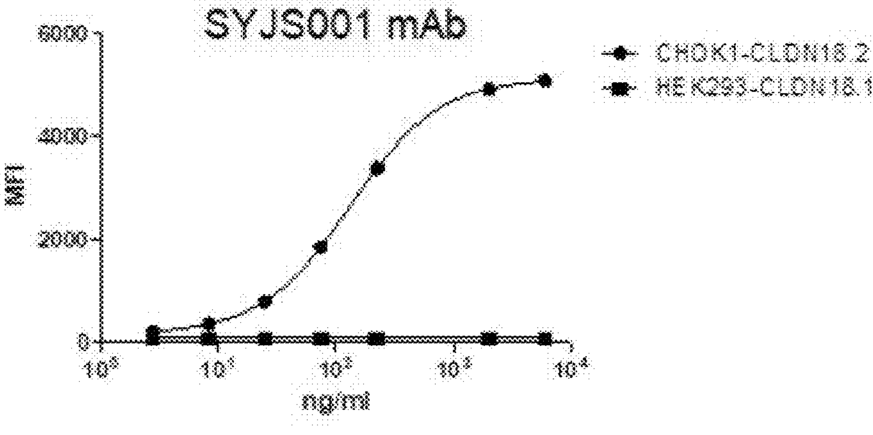
FIG. 9 shows the results of cross-reactivity experiment on SYJS001 antibody.
Figure 10:
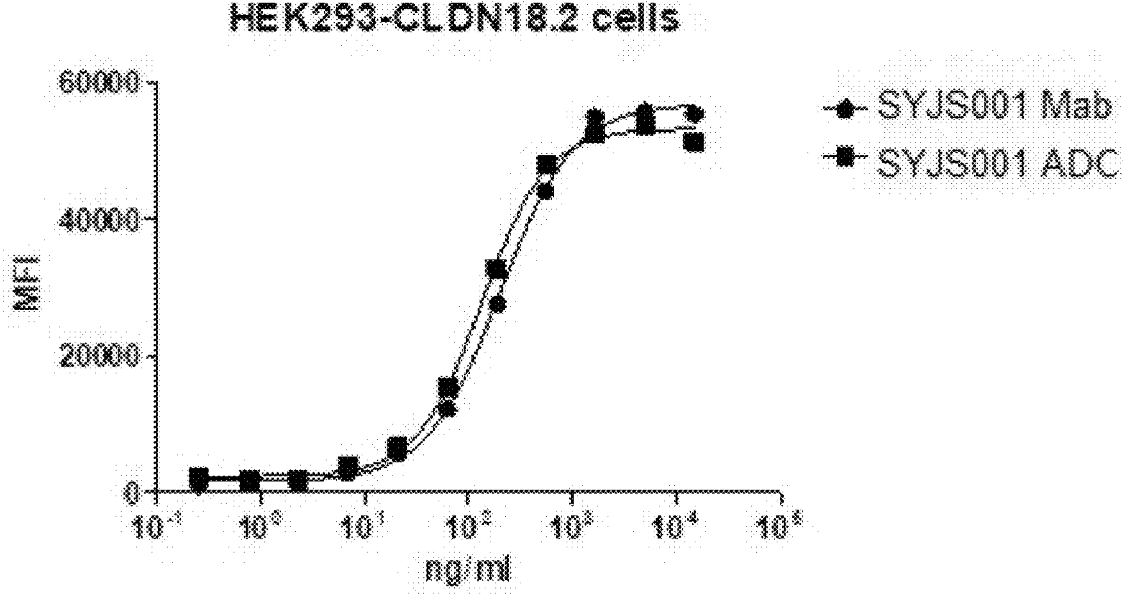
FIG. 10 shows the results of an assay of specific binding of SYJS001 ADC to CLDN18.2.

The results showed (see FIGS. 9 and 10) that, SYJS001 monoclonal antibody obtained in the present application was capable of specific binding to CLDN18.2 without significant cross-interaction with CLDN18.1. SYJS001 ADC also bound specifically to CLDN18.2 as compared to the naked antibody. No significant effect on antibody's affinity was observed after conjugation to toxins.

Example 7: Validation Experiment of SYJS001 ADC Endocytosis

Experimental Procedure

HEK293-CLDN18.2 cells were harvested and resuspended using DMEM complete medium. Cells were resuspended several times by gentle blowing to generate a single cell suspension. Cell viability and cell counts were determined using the trypan blue staining method. 100 μl of cell suspension with the cell density adjusted to $1\times10^5$ cells/ml was added into each well of a confocal 96-well cell culture plate. The number of cells per well was $1\times10^4$. SYJS001 labeled with Zenon™ pHrodo™ iFL was added to the 96-well plate at a final concentration of 2 μg/ml, and then the plate was continuously incubated at 37° C. in a 5% $CO_2$ incubator for 24 hours. All images were observed and taken by the laser confocal microscope 20× objective.

Figure 11:
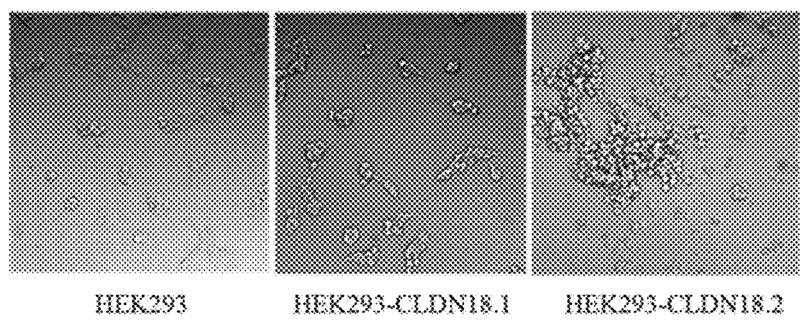
FIG. 11 shows endocytosis of SYJS001 ADC by HEK293-CLDN18.2 cells.
Figure 12:
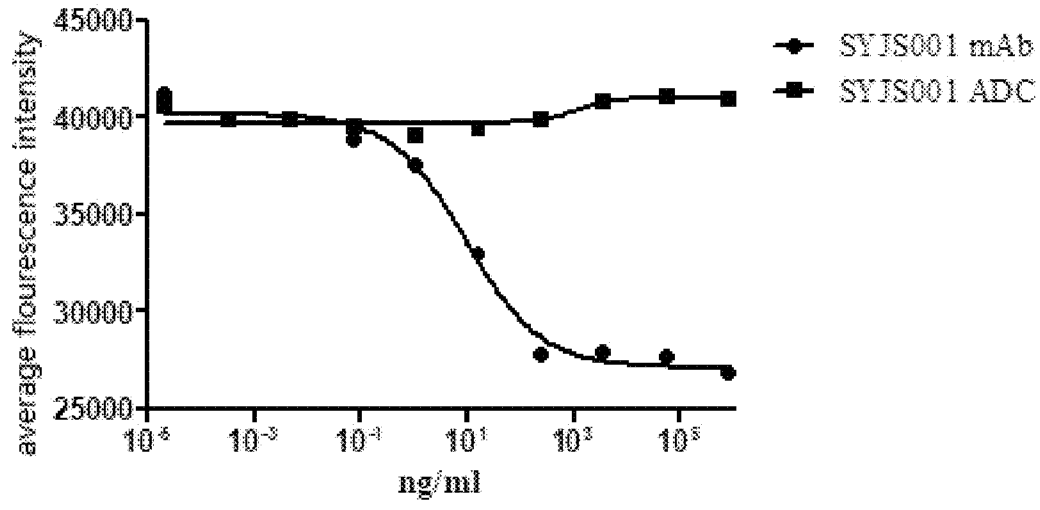
FIG. 12 shows the in vitro growth inhibitory effect of SYJS001 naked antibody and SYJS001 ADC on NCI-N87-CLDN18.2, where group 1 denotes SYJS001 ADC (square dots) and group 2 denotes SYJS001 naked antibody (circle dots).
Figure 13:
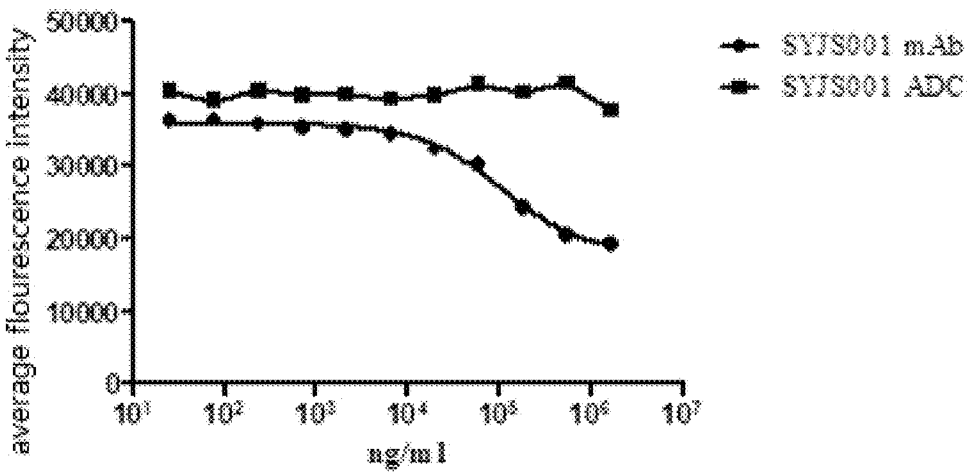
FIG. 13 shows the in vitro growth inhibitory effect of SYJS001 naked antibody and SYJS001 ADC on KATOIII, where group 1 denotes SYJS001 ADC (square dots) and group 2 denotes SYJS001 naked antibody (circle dots).
Figure 14:
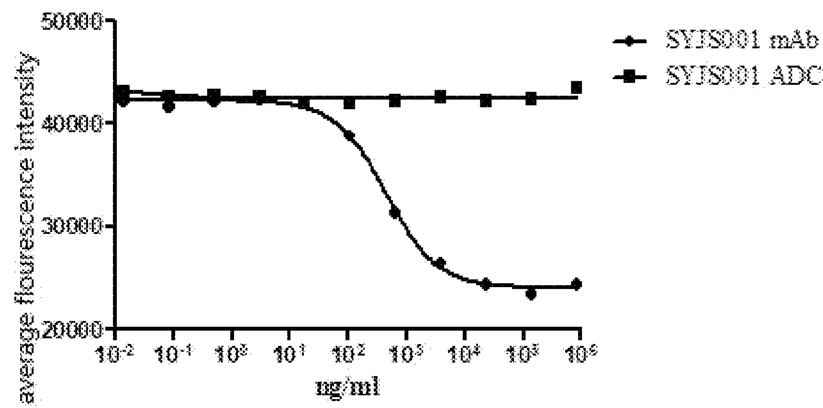
FIG. 14 shows the in vitro growth inhibitory effect of SYJS001 naked antibody and SYJS001 ADC on NCI-H460-CLDN18.2, where group 1 denotes SYJS001 ADC (square dots) and group 2 denotes SYJS001 naked antibody (circle dots).
Figure 15:
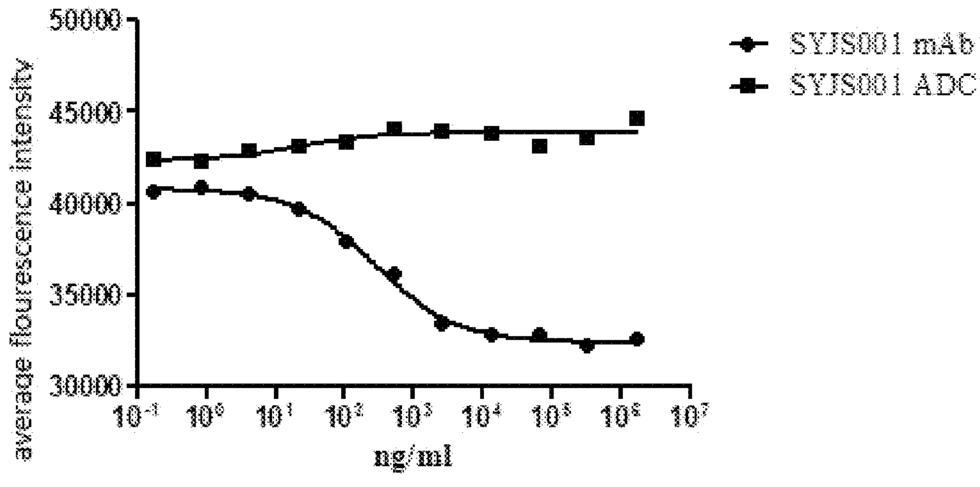
FIG. 15 shows the in vitro growth inhibitory effect of SYJS001 naked antibody and SYJS001 ADC on NUGC4-CLDN18.2, where group 1 denotes SYJS001 ADC (square dots) and group 2 denotes SYJS001 naked antibody (circle dots).
Figure 16:
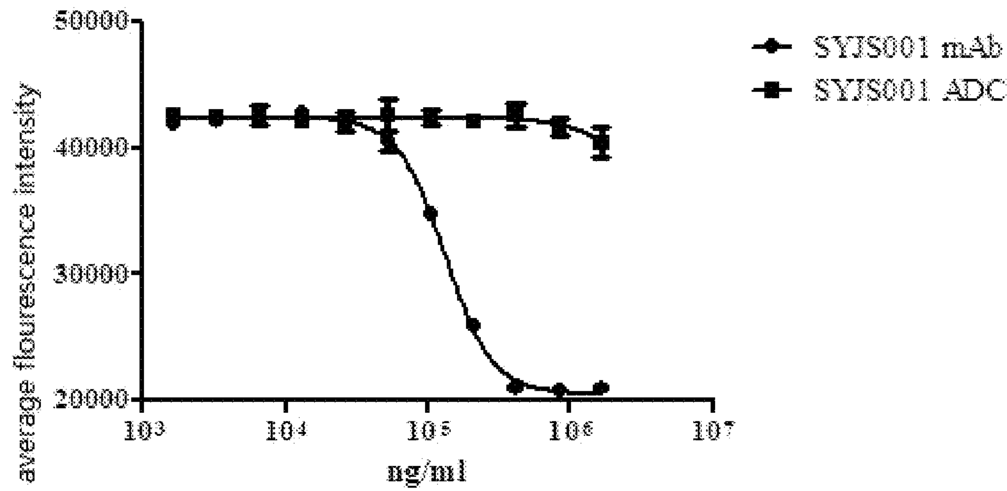
FIG. 16 shows the in vitro growth inhibitory effect of SYJS001 naked antibody and SYJS001 ADC on PATU8988S, where group 1 denotes SYJS001 ADC (square dots) and group 2 denotes SYJS001 naked antibody (circle dots).
Figure 17:
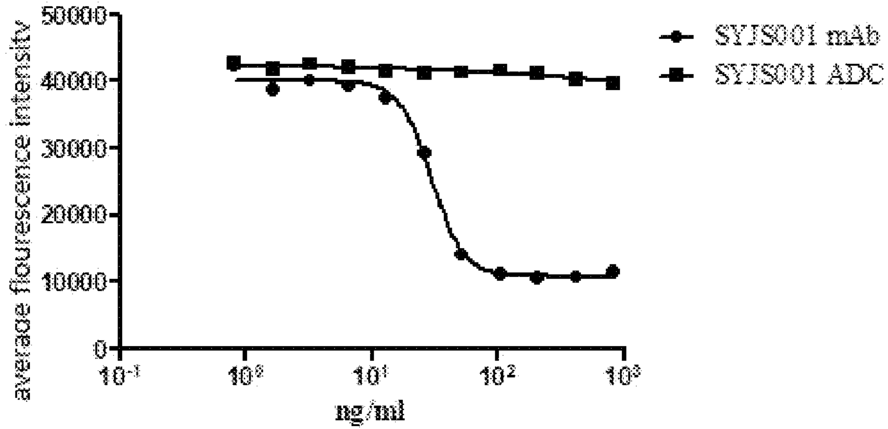
FIG. 17 shows the in vitro growth inhibitory effect of SYJS001 naked antibody and SYJS001 ADC on BxPC-3-

As shown in FIG. 11, the results showed that SYJS001 ADC was endocytosed by HEK293-CLDN18.2 cells, and localized in an acidic environment of lysosomes (Zenon™ pHrdo™ iFL IgG Labeling Reagents (Z25611) from Invitrogen only generated fluorescence in an acidic environment of lysosomes. For example, the parts enclosed by the three boxes in the rightmost panel (HEK293-CLDN18.2) of FIG. 11 showed green fluorescence points under the mirror), while endocytosis did not occur in the HEK293 and HEK293-CLDN18.1 cells, and no green fluorescence point was observed.

Example 8: Inhibition of Different Cell Growth by SYJS001 Naked Antibody and ADC Experimental Procedures: Cells were harvested for resuspension into single cell suspensions. Cell viability and cell counts were determined using the trypan blue staining method. 100 μl of cell suspension with the cell density adjusted to $1\times10^5$ cells/ml was added into each well of 96-well black flat bottom cell culture plates. 20 μl per well of diluted test samples was added to 96-well black flat bottom cell culture plates. The plates were incubated for 66±3 hr in a cell culture chamber (37° C., 5% $CO_2$). Sodium resazurin solution (w/v 0.03%) was added at 20 μl per well, and the plates were incubated for 3-4 h at 37° C. The fluorescence values were read by a microplate reader at 550 nm/610 nm and plotted using Magellan6 or similar plotting software to generate the half inhibitory concentrations $IC_{50}$ of the reference standard and test samples. The output parameter C is $IC_{50}$ in ng/mL.

As shown in FIGS. 12-17 and Table 4, SYJS001 ADC inhibited the growth of NCI-N87-CLDN18.2 (gastric cancer cell line), KATOIII (gastric cancer cell line), NCI-H460-CLDN18.2 (lung cancer cell line), NUGC4-CLDN18.2 (gastric cancer cell line), PATU8988S (pancreatic cancer cell line), and BxPC-3-CLDN18.2 (pancreatic cancer cell line) cancer cells in vitro.

TABLE 4

In vitro Proliferation Inhibition of Different Cells by SYJS001 naked antibody and SYJS001 ADC (Note: N/A = No Inhibition Effect)

| Compound Cell | $IC_{50}$ (ng/ml) | | | | | |
|---|---|---|---|---|---|---|
| | NCI-N87-CLDN18.2 | KATOIII | NCI-H460-CLDN18.2 | NUGC4-CLDN18.2 | PATU8988S | BxPC-3-CLDN18.2 |
| SYJS001 ADC | 7.04 ± 2.67 | 60526 ± 11976.97 | 456.94 ± 24.70 | 228.07 ± 43.95 | 769220 ± 11512 | 28.03 ± 0.89 |
| SYJS001 monoclonal antibody | N/A | N/A | N/A | N/A | N/A | N/A |

As shown above, SYJS001 ADC had a significant inhibitory effect on gastric cancer cells, lung cancer cells, and human pancreatic cancer cells that overexpressed CLDN18.2, and had a weak inhibitory effect on human gastric cancer cells KATOIII and human pancreatic cancer cells PATU8988S that did not express or underexpressed CLDN18.2.

Example 9: Assessment of In Vivo Efficacy of SYJS001 ADC 9.1 Efficacy Comparison with Gemcitabine and Cisplatin as References 1) In this experiment, nude mice with human pancreatic cancer Bxpc3-18.2 xenografts were used. When the tumor volume reached about 100 $mm^3$ (day 39 after inoculation), 48 animals with bulky xenografts were selected and divided into six groups (on day 0) with tumor volume balancing among groups. Eight animals in individual groups were intravenously administered 0.9% sodium chloride injection (0.9% INJ NS, vehicle control group), SYJS001-ADC at 2, 4 and 8 mg/kg (single dose), SYJS001-mAb (SYJS001 nude antibody) at 8 mg/kg (single dose) and Gemcitabine (GEM) at 50 mg/kg (biw×4, twice a week for 4 weeks), respectively. Tumor diameters were measured twice a week. Mice were weighed, and data were recorded. Tumor growth was dynamically observed by measuring tumor diameters at different times after dosing. At the end of the experiment on day 28, the mice were asphyxiated with carbon dioxide, and the tumors were peeled and weighed.

The following results were got in this experiment. The tumor weight suppression rates were 56.6%, 94.8%, 97.8%, −36.2%, 51.0% in the groups of SYJS001-ADC at 2, 4, and 8 mg/kg (single dose), SYJS001-mAb at 8 mg/kg (single dose) group, and Gemcitabine at 50 mg/kg (biw×4), respectively. SYJS001-ADC at 2, 4 and 8 mg/kg (single dose) and GEM at 50 mg/kg (biw×4: twice a week, total of four doses) significantly inhibited tumor growth, as compared with the vehicle control group (0.9% sodium chloride injection) ($P<0.01$). The tumor suppression was more pronounced in the groups of SYJS001-ADC at 4 and 8 mg/kg (single dose) than in the positive control group of GEM at 50 mg/kg (biw×4) group. Particularly, the group of SYJS001-ADC at 8 mg/kg had a nearly 2-fold suppression rates ($p<0.001$) (see FIG. 18).

2) In this experiment, nude mice with human gastric cancer NUGC-4-18.2 xenografts were used. When the tumor volume reached about 120 mm$^3$ (day 6 after inoculation), 64 animals with bulky xenografts were selected and divided into eight groups (on day 0) with tumor volume balancing among groups. Eight animals in individual groups were intravenously administered 0.9% sodium chloride injection (0.9% INJ NS, vehicle control group), SYJS001-ADC at 1, 2 and 4 mg/kg (qw×3), SYJS001-ADC at 4 and 8 mg/kg (single dose), SYJS001-mAb at 4 mg/kg (qw×3) and Cisplatin at 6 mg/kg (qw×3, once a week for 3 weeks), respectively. Tumor diameters were measured twice a week. Mice were weighed, and data were recorded. Tumor growth was dynamically observed by measuring tumor diameters at different times after dosing. At the end of the experiment on day 20, the mice were asphyxiated with carbon dioxide, and the tumors were peeled and weighed.

The following results were got in this experiment. The tumor weight suppression rates were 98.0%, 100%, 100%, 100%, 100%, −1.2%, 66.5% in the groups of SYJS001-ADC at 1, 2, 4 mg/kg (qw×3), SYJS001-ADC at 4, 8 mg/kg (single dose), SYJS001-mAb at 4 mg/kg (qw×3), and Cisplatin at 6 mg/kg (qw×3), respectively. As compared with the vehicle control group, the tumor growth was significantly inhibited in all test groups (P<0.001) except for the group of SYJS001-mAb at 4 mg/kg (qw×3). The group of SYJS001-ADC at 1, 2, 4 mg/kg (qw×3) and SYJS001-ADC at 4 and 8 mg/kg (single dose) showed significant advantage over the positive control group of Cisplatin 6 mg/kg (qw×3) in terms of efficacy and toxicity (P<0.05) (see FIG. 19).

9.2 Efficacy Comparison with IMAB362-ADC as Reference

IMAB362 (also known as claudiximab or zolbetuximab) is a known chimeric monoclonal antibody of IgG1 subtype that selectively targets the first extracellular domain of CLDN18.2 and has little activity against CLDN18.1. IMAB362 was selected as a reference antibody in this experiment.

1) In the present experiment, nude mice with human pancreatic cancer Bxpc3-18.2 xenografts were used. When the tumor volume reached about 100 mm$^3$ (day 39 after inoculation), 64 animals with bulky xenografts were selected and divided into eight groups (on day 0) with tumor volume balancing among groups. Eight animals in individual groups were intravenously administered 0.9% sodium chloride injection (0.9% INJ NS, vehicle control group), SYJS001-ADC at 2, 4 and 8 mg/kg (single dose), IMAB362-ADC (The sequence of IMAB362 is from CN201680021997.6. Gene synthesis was performed by Nanjing GenScript Biotechnology Co., Ltd. Protein expression was done by transient expression using the KOP293 transient transfection protein expression system from Zhuhai Kailui Biotechnology Co., Ltd (see website for detailed steps). IMAB362-ADC was prepared according to the method in Example 3, Method of Preparation of SYJS001 ADC) at 2, 4 and 8 mg/kg (single dose), and SYJS001-mAb at 8 mg/kg (single dose), respectively. Tumor diameters were measured twice a week. Mice were weighed, and data were recorded. Tumor growth was dynamically observed by measuring tumor diameters at different times after dosing. At the end of the experiment on day 28, the mice were asphyxiated with carbon dioxide, and the tumors were peeled and weighed.

The following results were got in this experiment. Where tumor volume of the vehicle control group serves as 100%, the percent tumor volumes of the groups of SYJS001-ADC at 2, 4 and 8 mg/kg (single dose), SYJS001-mAb at 8 mg/kg (single dose) and IMAB362-ADC at 2, 4 and 8 mg/kg (single dose) were 35.9%, 6.0%, 3.4%, 116.2%, 47.0%, 6.8% and respectively. SYJS001-ADC at 2, 4 and 8 mg/kg (single dose) and IMAB362-ADC at 2, 4 and 8 mg/kg (single dose) significantly inhibited tumor growth, as compared with the vehicle control group (p<0.01). For SYJS001-ADC vs. the positive reference IMAB362-ADC, their effects were comparable at the high dose, but the in vivo anti-tumor effect of SYJS001 ADC was significantly better than that of IMAB362-ADC at the low dose (starting dose). See, FIG. for RTV (relative tumor volume) data.

According to data published in Chunze Li 2019 (Clinical pharmacology of vc-MMAE antibody-drug conjugates in cancer patients: learning from eight first-in-human Phase 1 studies 2019 vol. 12, No. 1, MABS), the VC-MMAE-based ADCs generally have a clinical administration dose range of 0.1-3.2 mg. Therefore, the low dose of the present experiment is more promising in the prospect of clinical application, and therefore the clinical prospect and drug development of SYJS001-ADC is superior to IMAB362-ADC.

2) In this experiment, nude mice with human gastric cancer NUGC-4-18.2 xenografts were used. When the tumor volume reached about 120 mm$^3$ (day 6 after inoculation), 64 animals with bulky xenografts were selected and divided into eight groups (on day 0) with tumor volume balancing among groups. Eight animals in individual groups were intravenously administered 0.9% sodium chloride injection (0.9% INJ NS, vehicle control group), SYJS001-ADC at 0.5, 1, 2 and 4 mg/kg (single dose), IMAB362-ADC at 0.5, 1, 2 and 4 mg/kg (single dose), and SYJS001-mAb at 4 mg/kg (single dose), respectively. Tumor diameters were measured twice a week. Mice were weighed, and data were recorded. Tumor growth was dynamically observed by measuring tumor diameters at different times after dosing. At the end of the experiment on day 20, the mice were asphyxiated with carbon dioxide, and the tumors were peeled and weighed.

The following results were got in this experiment. Where tumor volume of the vehicle control group serves as 100%, the percent tumor volumes of the groups of SYJS001-ADC at 0.5, 1, 2 and 4 mg/kg (single dose), IMAB362-ADC at 0.5, 1, 2 and 4 mg/kg (single dose), and SYJS001-mAb at 4 mg/kg (single dose) were 59.1%, 27.3%, 1.8%, 0%, 68.2%, 30%, 1.8%, 0%, and 83.6%, respectively. As compared with the vehicle control group, the tumor growth was significantly inhibited in all test groups except for the group of SYJS001-mAb at 4 mg/kg (p<0.001). For SYJS001-ADC vs. IMAB362-ADC in the in vivo anti-tumor effect directed to NUGC-4-18.2, their effects were comparable at the high dose, but the in vivo anti-tumor effect of SYJS001 ADC was significantly better than that of IMAB362-ADC at the low dose (starting dose). See, FIG. 21.

Similar to the preceding comparative experiment, the low dose of the present experiment is more promising in the prospect of clinical application, and therefore the clinical prospect and drug development of SYJS001-ADC is superior to IMAB362-ADC.

Example 10: MMAE Release and Bystander Effect Test

After 4 days of co-culture of positive group BxPC-3-CLDN18.2 and HEK293-Luc cells (cells not expressing CLDN18.2) with SYJS001 ADC, the number of HEK293-Luc cells in the cell mixture was indicated by chemiluminescence development. As compared with the negative group, i.e. the BxPC-3 and HEK293-Luc co-culture group, three concentrations including 5 μg/ml, 1 μg/ml, and 200 ng/ml were able to cause proliferation inhibition of HEK293-Luc cells to various extents. This indicated that SYJS001 was able to bind to the positive group BxPC-3-Human CLDN18.2 ADC and then entered the cells by endocytosis. MMAE released in the cells was able to lead to apoptosis of BxPC-3-human CLDN18.2. MMAE released after cellular apoptosis and lysis was able to cause growth inhibition of bystander cells, as shown in FIG. 22. Thus, MMAE could be efficiently released from SYJS001 ADC and exerted cytotoxic activity on neighboring cells due to its membrane permeability, demonstrating a bystander effect.

In view of the results from above multiple Examples, it can be seen that the anti-CLDN18.2 monoclonal antibody obtained in the present application specifically binds to CLDN18.2 positive cells and leads to highly efficient internalization. The ADC drug obtained in the present application has an extremely strong killing effect on tumor cells represented by pancreatic cancer, gastric cancer, and lung cancer.

Example 11: Assessment of ADC Stability

11.1 Stability Test in Plasma and Serum

The object of this experimental study was to investigate the in vitro metabolic stability of SYJS001-ADC in plasma and serum from different species (human, cynomolgus monkey and SD rat). SYJS001-ADC was incubated at a concentration of 10011 g/mL for 0-168 h (7 days) at 37° C. under sterile conditions. The concentration of MMAE in 0.5% BSA-PBS, human plasma, cynomolgus monkey plasma, and SD rat plasma was measured by a LC-MS/MS method. The results were shown in Tables 5 to 8. Free MMAE was produced in all substrates with increasing incubation time. After SYJS001-ADC was incubated for 168 h (7 days) at 37° C., the shedding percentages in 0.5% BSA-PBS, human plasma, cynomolgus monkey plasma and SD rat plasma were 0.672%, 0.327%, 0.209% and 0.405%, respectively. The experiment showed that SYJS001-ADC has an MMAE shedding rate of less than 1.0%, indicating that SYJS001-ADC was relatively stable in 0.5% BSA-PBS, human plasma, cynomolgus monkey plasma and SD rat plasma.

TABLE 5

Concentration of free MMAE and shedding rate from ADC in 0.5% BSA-PBS solution

| | Time (h) | Concentration (ng/mL) 1 | 2 | 3 | Average | Standard deviation | shedding rate (%) |
|---|---|---|---|---|---|---|---|
| 0.5% BSA-PBS | 0 | 0.167 | 0.179 | 0.154 | 0.167 | 0.013 | 0.017 |
| | 8 | 0.662 | 0.635 | 0.682 | 0.660 | 0.024 | 0.069 |
| | 24 | 1.687 | 1.791 | 1.711 | 1.730 | 0.054 | 0.181 |
| | 48 | 2.808 | 2.732 | 2.871 | 2.804 | 0.070 | 0.293 |
| | 72 | 3.485 | 3.536 | 3.457 | 3.493 | 0.040 | 0.365 |
| | 96 | 4.532 | 4.446 | 4.238 | 4.405 | 0.151 | 0.460 |
| | 168 | 5.51 | 6.846 | 6.951 | 6.436 | 0.803 | 0.672 |

TABLE 6

Concentration of free MMAE and shedding rate from ADC in in human plasma

| | Time (h) | Concentration (ng/mL) 1 | 2 | 3 | Average | Standard deviation | shedding rate (%) |
|---|---|---|---|---|---|---|---|
| Human plasma | 0 | BQL | BQL | BQL | BQL | NA | NA |
| | 8 | 0.105 | 0.106 | 0.097 | 0.103 | 0.005 | 0.011 |
| | 24 | 0.39 | 0.33 | 0.31 | 0.343 | 0.042 | 0.036 |
| | 48 | 0.695 | 0.713 | 0.631 | 0.680 | 0.043 | 0.071 |
| | 72 | 1.05 | 1.045 | 0.932 | 1.009 | 0.067 | 0.105 |
| | 96 | 1.398 | 1.34 | 1.193 | 1.310 | 0.106 | 0.137 |
| | 168 | 3.017 | 3.122 | 3.238 | 3.126 | 0.111 | 0.327 |

TABLE 7

Concentration of free MMAE and shedding rate from ADC in monkey plasma

| | Time (h) | Concentration (ng/mL) 1 | 2 | 3 | Average | Standard deviation | shedding rate (%) |
|---|---|---|---|---|---|---|---|
| Monkey plasma | 0 | BQL | BQL | BQL | BQL | NA | NA |
| | 8 | 0.118 | 0.137 | 0.138 | 0.131 | 0.011 | 0.014 |
| | 24 | 0.304 | 0.25 | 0.299 | 0.284 | 0.030 | 0.030 |
| | 48 | 0.549 | 0.556 | 0.543 | 0.549 | 0.007 | 0.057 |
| | 72 | 0.773 | 0.773 | 0.671 | 0.739 | 0.059 | 0.077 |
| | 96 | 1.042 | 0.971 | 0.978 | 0.997 | 0.039 | 0.104 |
| | 168 | 1.97 | 2.05 | 1.983 | 2.001 | 0.043 | 0.209 |

TABLE 8

Concentration of free MMAE and shedding rate from ADC in rat plasma

| | Time (h) | Concentration (ng/mL) 1 | 2 | 3 | Average | Standard deviation | shedding rate (%) |
|---|---|---|---|---|---|---|---|
| Rat plasma | 0 | BQL | BQL | BQL | BQL | NA | NA |
| | 8 | 0.24 | 0.217 | 0.2 | 0.219 | 0.020 | 0.023 |
| | 24 | 0.565 | 0.537 | 0.532 | 0.545 | 0.018 | 0.057 |
| | 48 | 1.064 | 1.002 | 1.042 | 1.036 | 0.031 | 0.108 |
| | 72 | 1.498 | 1.393 | 1.538 | 1.476 | 0.075 | 0.154 |
| | 96 | 2.09 | 2.009 | 1.883 | 1.994 | 0.104 | 0.208 |
| | 168 | 4.041 | 3.801 | 3.793 | 3.878 | 0.141 | 0.405 |

11.2 Accelerated Stability Test

SYJS001-ADC was stored in buffer (5 w/v % L-histidine, and 25 w/v % L-histidine hydrochloride) at 2° C. to 8° C. for different periods and tested for stability. The results are shown in the following table. IMAB362-ADC (IMAB362-vcMMAE) yielded 0.3% of free toxin on day 28 (see Table 7 in CN 107667118A), which is much higher than 0.000026%, i.e., free toxin percentages from SYJS001-ADC of the present application after storage for 3 months, indicating that SYJS001-ADC was much more stable than IMAB362-ADC.

TABLE 9

Accelerated stability (6° C. ± 2° C.) test results of SYJS001-ADC

| Item | Time (months)-SYJS001-ADC Month 0 | Month 1 | Month 2 | Month 3 |
|---|---|---|---|---|
| DAR | DAR: 2.01 | 2.01 | 2.00 | 2.00 |
| distribution | DAR2: 76.80% | 77.83% | 78.50% | 77.29% |
| Free MMAE | 0.000012% | 0.000018% | 0.000020% | 0.000026% |
| Free L&D | <0.004% | <0.004% | <0.004% | <0.004% |

Example 12: Comparative Study of SYJS001 and IMAB362

12.1 Affinity

CLDN18.2-overexpressing cell line BxPC3-CLDN18.2 was resuspended in a PBS buffer and 100 μl per well of a cell suspension with cell density adjusted to $1\times10^6$ cells/ml was added to 96-well V-type culture plates. The plates were centrifuged at 2500 rpm for 5 min and the supernatant was discarded. The test samples were diluted with an experimental buffer at a starting concentration of 40 μg/ml with a 5-fold gradient of 10 gradients. 100 μl per well of test sample dilutions was added to 96-well V-shaped plates and the plates were incubated at 4° C. for 60~90 minutes. At the end of incubation, the plates were placed in a centrifuger and centrifuged at 2500 rpm for 5 min. After centrifuging, the supernatant was carefully shaken off, and the cells were resuspended in 100 μl of PBS buffer and centrifuged at 2500 rpm for 5 min. The operations were repeated twice. After centrifuging, the supernatant was carefully shaken off, and the fluorescent antibody detection reagent (1:1000 dilution) was added according to the experimental arrangement, and the plates were incubated at 4° C. for 30~60 minutes in the dark. At the end of incubation, the plates were placed in a high-speed centrifuger and centrifuged at 2500 rpm for 5 min. After centrifuging, the supernatant was carefully shaken off, and the cells were resuspended in 100 μl of assay buffer and then detected by flow cytometry using a plate reader to read the fluorescence signal values of the corresponding wells in the assay plate. The experimental data were derived and analyzed using the GraphPad Prism 5 software. A regression model of the four-parameter equation was selected as the "S"-shaped curve and the software automatically generated the half effective amount $ED_{50}$ (C value). The results were shown below (FIG. 23, MFI: Mean Fluorescence Intensity). The affinity of SYJS001 is more than twice that of IMAB362.

12.2 Epitope Characterization

Epitope competition of SYJS001-ADC with IMAB362-ADC was detected with Octet epitope pairing. 5 μg/ml of human CLDN18.2 protein was used to coat the HIS1K capture sensors, and loaded for 180 s. The two antibodies were diluted to 100 nM, respectively, and the coated sensors were first allowed to bind to one of the antibodies (Association) for 180 s and then to the second antibody (Association) for 180 s. The binding signal of the second antibody was detected to determine whether the two antibodies recognized the same epitope. Results: 60%-100% represents no competition at all; 20%-60% represents partial competition; and <20% represents completely competitive, i.e., two antibodies were considered competitive. The results are shown in the table below (Table 10), where the SYJS001-ADC and IMAB362-ADC had completely competitive epitopes.

TABLE 10

| | SYJS001 | IMAB362 |
|---|---|---|
| SYJS001 | 9.02% | 7.98% |
| IMAB362 | 7.88% | 6.6% |

12.3 Endocytosis Detection

BxPC3-CLDN18.2 cells were seeded in 6-well plates with approximately $4\text{-}6\times10^5$ cells per well. The plates were placed in an incubator and incubated overnight at 37° C. and 5% $CO_2$. The antibody was diluted to 5 μg/ml with a complete medium (DMEM (Hyclone, Cat. No. SH30243.01)+10% FBS (Gibco, Cat. No. 10091-148)+1 μg/ml of puromycin (Gibco, Cat. No. A11138-02)). The remaining medium in the 6-well plates was discarded, and 2 ml of the complete medium containing the antibody was added to each well. The plates were incubated for 2 hr at 4° C., and the supernatant was discarded. The plates were washed twice with the complete medium. 2 ml of antibody-free complete medium was added to each well. 2-3 duplicate wells were taken for trypsinization at this time point as the total amount of antibody bound by the cells. The remaining cells were transferred to an incubator and allowed for endocytosis for 4 hr, 21 hr, 25 hr and 48 hr at 37° C. in a 5% $CO_2$ incubator. After the trypsinized cells at each time point were washed, fluorescent antibody detection reagent (1:1000 dilution) was added and the plates were incubated at 4° C. for 60 minutes in the dark. After centrifuging, the supernatant was carefully dumped. After the plates were washed twice, the fluorescence signal value was detected by flow cytometry.

Endocytosis Rate=(Total antibody fluorescence signal-fluorescence signal at different time points)/total antibody fluorescence signal×100%. The results are shown below (FIG. 24, MFI: Mean fluorescence intensity). The endocytosis rate of SYJS001 at the early stage (0-21 hr) was significantly higher than that of IMAB362-ADC. At 21-48 hr, the endocytosis rate of SYJS001 was substantially consistent with that of IMAB362-ADC. Under same conditions, a better endocytosis rate leads to stronger ability of the drug to enter tumor cells, such that toxic molecules can be released better, and the faster acting effect is objectively achieved. SYJS001 is therefore expected to act faster than IMAB362-ADC.

12.4 In Vitro Cell Growth Inhibition Assay

1. Adenocarcinoma Cell Model

BxPC-3-CLDN18.2 cells were harvested and resuspended using complete medium (as used in part 12.3 endocytosis assay). Cells were resuspended several times by gentle blowing to generate a single cell suspension. Cell viability and cell counts were determined using the trypan blue staining method. 100 μl of cell suspension with the cell density adjusted to $1\times10^5$ cells/ml was added into each well of 96-well black flat bottom cell culture plates. The antibody at a starting concentration of 5 μg/ml was diluted with a 2-fold gradient for a total of 11 gradients. 20 μl per well of diluted test samples was added to 96-well black flat bottom cell culture plates having seeded cells. The antibody and cells were co-cultured and incubated in a cell incubator (37° C., 5% $CO_2$) for 63-69 hr. After incubation, 20 μl per well of resazurin sodium solution (w/v 0.03%) was added, and the plates were incubated for 3-4 h at 37° C. The fluorescence values were read by a microplate reader at 550 nm/610 nm and plotted using Magellan6 or similar plotting software to generate the half inhibitory concentration $IC_{50}$ of the reference standards and test samples. The output parameter C is $IC_{50}$ in ng/mL. The results are shown below (FIG. 25, RLU: Relative Luminescence Units). The in vitro inhibitory effect of SYJS001-ADC on BxPC-3-CLDN18.2 cells is significantly superior to that of IMAB362-ADC.

2. Gastric Cancer Cell Model

NUGC4-CLDN18.2 cells were harvested and resuspended using complete medium (as used in part 12.3 endocytosis assay). Cells were resuspended several times by gentle blowing to generate a single cell suspension. Cell viability and cell counts were determined using the trypan blue staining method. 100 μl of cell suspension with the cell density adjusted to $1\times10^5$ cells/ml was added into each well of 96-well black flat bottom cell culture plates. The antibody at a starting concentration of 5 μg/ml was diluted with a 2-fold gradient for a total of 11 gradients. 20 μl per well of diluted test samples was added to 96-well black flat bottom cell culture plates having seeded cells. The antibody and cells were co-cultured and incubated in a cell incubator (37° C., 5% $CO_2$) for 63-69 hr. After incubation, 20 μl per well of resazurin sodium solution (w/v 0.03%) was added, and the plates were incubated for 3-4 h at 37° C. The fluorescence values were read by a microplate reader at 550 nm/610 nm and plotted using Magellan6 or similar plotting software to generate the half inhibitory concentration $IC_{50}$ of the reference standards and test samples. The output parameter C is $IC_{50}$ in ng/mL. The results are shown below (FIG. 25, RLU: Relative Luminescence Units). The in vitro inhibitory effect of SYJS001-ADC on NUGC4-CLDN18.2 cells was superior to (more than 2-fold) that of IMAB362-ADC.

In view of the above experiments, SYJS001-ADC obtained in the present application is significantly superior to the control IMAB362-ADC in terms of stability, antibody affinity, endocytosis efficiency, and tumor cell inhibition in vitro and in vivo.

The above description merely illustrates preferred embodiments, which are by way of example only and do not limit the combination of features necessary to practice the present application. The headings provided are not intended to limit the various embodiments of the present application. Terms such as “comprising,” “containing” and “including” are not intended to be limiting. Further, unless otherwise indicated, lack of numerical modification includes the plural form. “Or” means “and/or”. Unless defined otherwise herein, all technical and scientific terms used herein have the same meaning as commonly understood by one skilled in the art. All publications and patents cited in the present application are incorporated herein by reference. Various modifications and variations of the methods and compositions described herein will be apparent to those skilled in the art without departing from the scope and spirit of the present application. While the present application has been described by specific preferred embodiments, it is to be understood that the claimed application should not be unduly limited to these specific embodiments. Indeed, various variations of the described embodiments for carrying out the present application, which will be apparent to those skilled in the relevant art, are intended to be included within the scope of the appended claims.

The invention claimed is:

1. A conjugate, comprising an antibody or an antigen-binding fragment thereof conjugated with one or more drug molecules, wherein the antibody comprises a heavy chain and a light chain, and the heavy chain comprises three CDR regions having the amino acid sequences as set forth in SEQ ID NOs: 1, 2 and 3 respectively and the light chain comprises three CDR regions having the amino acid sequences as set forth in SEQ ID NOs: 4, 5 and 6 respectively, wherein the drug molecule is MMAE (Monomethyl auristatin E), the drug molecule is conjugated with the antibody or antigen-binding fragment thereof via a linker, which is linked to the antibody or antigen-binding fragment via an amino group, and the linker is $NH_2$—($CH_2$—$CH_2$—O)$_m$—$CH_2$—C(═O)—Val-Cit-p-aminobenzyloxycarbonyl (pABC), wherein m is an integer from 1 to 8, and the average drug antibody ratio is 2.

2. The conjugate of claim 1, wherein the antibody is a monoclonal antibody, a bispecific antibody, or a fully human monoclonal antibody.

3. The conjugate of claim 1, wherein the heavy chain comprises a heavy chain variable region having the amino acid sequence as set forth in SEQ ID NO: 7, and/or the light chain comprises a light chain variable region having the amino acid sequence as set forth in SEQ ID NO:8.

4. The conjugate of claim 1, wherein the heavy chain comprises the amino acid sequence as set forth in SEQ ID NO:9, and/or the light chain comprises the amino acid sequence as set forth in SEQ ID NO: 10.

5. The conjugate of claim 1, wherein m is 3.

6. A pharmaceutical composition comprising the conjugate of claim 1, and a pharmaceutically acceptable carrier.

7. A method of treating cancer in a subject, comprising administering to the subject in need thereof a therapeutically effective amount of the conjugate of claim 1.

8. The method of claim 7, wherein the cancer is CLDN18.2 positive cancer.

9. The method of claim 7, wherein the cancer is gastric cancer, esophageal cancer, pancreatic cancer, lung cancer, ovarian cancer, colon cancer, liver cancer, head and neck cancer, or gallbladder cancer.

10. The method of claim 7, wherein the cancer is an adenocarcinoma of stomach, esophagus, pancreatic duct, bile duct, lung, or ovary.

11. The method of claim 7, wherein the cancer is gastric cancer or pancreatic cancer.

12. A method of treating a tumor in a subject, comprising administering to the subject in need thereof a therapeutically effective amount of the conjugate of claim 1 and an antiproliferative agent.

13. The method of claim 12, wherein the antiproliferative agent is selected from the group consisting of paclitaxel, doxorubicin, docetaxel, cisplatin, carboplatin, and iproplatin.

14. A kit comprising a container containing the conjugate of claim 1.

* * * * *

SEQUENCE LISTING

```
<160> NUMBER OF SEQ ID NOS: 20

<210> SEQ ID NO 1
<211> LENGTH: 8
<212> TYPE: PRT
<213> ORGANISM: Artificial Sequence
<220> FEATURE:
<223> OTHER INFORMATION: HCDR1

<400> SEQUENCE: 1

Gly Phe Thr Phe Ser Ser Tyr Ala
1               5


<210> SEQ ID NO 2
<211> LENGTH: 8
<212> TYPE: PRT
<213> ORGANISM: Artificial Sequence
<220> FEATURE:
<223> OTHER INFORMATION: HCDR2

<400> SEQUENCE: 2

Leu Ser Gly Ser Gly Arg Ser Thr
1               5


<210> SEQ ID NO 3
<211> LENGTH: 13
<212> TYPE: PRT
<213> ORGANISM: Artificial Sequence
<220> FEATURE:
<223> OTHER INFORMATION: HCDR3

<400> SEQUENCE: 3

Ala Lys Ser Leu Ser Tyr Tyr His Tyr Tyr Phe Asp Tyr
1               5                   10
```

<210> SEQ ID NO 4
<211> LENGTH: 6
<212> TYPE: PRT
<213> ORGANISM: Artificial Sequence
<220> FEATURE:
<223> OTHER INFORMATION: LCDR1

<400> SEQUENCE: 4

Gln Asp Ile Ser Asn Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: LCDR2

<400> SEQUENCE: 5

Ser Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln Gln Val Lys Thr Tyr Pro Leu Thr
1               5

<210> SEQ ID NO 7
<211> LENGTH: 120
<212> TYPE: PRT
<213> ORGANISM: Artificial Sequence
<220> FEATURE:
<223> OTHER INFORMATION: Heavy Chain Variable Region

<400> SEQUENCE: 7

Glu Val Gln Leu Ser Glu Ser Gly Gly Ala Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ser Leu Ser Gly Ser Gly Arg Ser Thr Tyr Tyr Ala Ala Ser Ile
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Ile Tyr Tyr Cys
                85                  90                  95

Ala Lys Ser Leu Ser Tyr Tyr His Tyr Tyr Phe Asp Tyr Trp Gly Gln
            100                 105                 110

Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Light Chain Variable Region

<400> SEQUENCE: 8

```
Asp Ile Gln Leu Thr Gln Ser Pro Ser Phe Leu Ser Ala Ser Val Gly
1               5                   10                  15

Asp Arg Val Pro Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr His Cys Gln Gln Val Lys Thr Tyr Pro Leu
                85                  90                  95

Thr Phe Gly Gly Gly Thr Lys Val Glu Ile Lys
            100                 105
```

<210> SEQ ID NO 9
<211> LENGTH: 450
<212> TYPE: PRT
<213> ORGANISM: Artificial Sequence
<220> FEATURE:
<223> OTHER INFORMATION: Heavy Chain

<400> SEQUENCE: 9

```
Glu Val Gln Leu Ser Glu Ser Gly Gly Ala Leu Val Gln Pro Gly Glu
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ser Leu Ser Gly Ser Gly Arg Ser Thr Tyr Tyr Ala Ala Ser Ile
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Ile Tyr Tyr Cys
                85                  90                  95

Ala Lys Ser Leu Ser Tyr Tyr His Tyr Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 10
<211> LENGTH: 214
<212> TYPE: PRT
<213> ORGANISM: Artificial Sequence
<220> FEATURE:
<223> OTHER INFORMATION: Light Chain

<400> SEQUENCE: 10

Asp Ile Gln Leu Thr Gln Ser Pro Ser Phe Leu Ser Ala Ser Val Gly
1               5                   10                  15

Asp Arg Val Pro Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr His Cys Gln Gln Val Lys Thr Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 11
<211> LENGTH: 25
<212> TYPE: PRT
<213> ORGANISM: Artificial Sequence
<220> FEATURE:
<223> OTHER INFORMATION: FR-H1

<400> SEQUENCE: 11

Glu Val Gln Leu Ser Glu Ser Gly Gly Ala Leu Val Gln Pro Gly Glu
1               5                   10                  15

Ser Leu Arg Leu Ser Cys Ala Ala Ser
            20                  25


<210> SEQ ID NO 12
<211> LENGTH: 17
<212> TYPE: PRT
<213> ORGANISM: Artificial Sequence
<220> FEATURE:
<223> OTHER INFORMATION: FR-H2

<400> SEQUENCE: 12

Met Thr Trp Val Arg Gln Ala Pro Gly Lys Gly Leu Glu Trp Val Ser
1               5                   10                  15

Ser


<210> SEQ ID NO 13
<211> LENGTH: 38
<212> TYPE: PRT
<213> ORGANISM: Artificial Sequence
<220> FEATURE:
<223> OTHER INFORMATION: FR-H3

<400> SEQUENCE: 13

Tyr Tyr Ala Ala Ser Ile Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Ile Tyr Tyr Cys
        35


<210> SEQ ID NO 14
<211> LENGTH: 11
<212> TYPE: PRT
<213> ORGANISM: Artificial Sequence
<220> FEATURE:
<223> OTHER INFORMATION: FR-H4

<400> SEQUENCE: 14

Trp Gly Gln Gly Thr Leu Val Thr Val Ser Ser
1               5                   10
```

```
<210> SEQ ID NO 15
<211> LENGTH: 26
<212> TYPE: PRT
<213> ORGANISM: Artificial Sequence
<220> FEATURE:
<223> OTHER INFORMATION: FR-L1

<400> SEQUENCE: 15

Asp Ile Gln Leu Thr Gln Ser Pro Ser Phe Leu Ser Ala Ser Val Gly
1               5                   10                  15

Asp Arg Val Pro Ile Thr Cys Arg Ala Ser
            20                  25


<210> SEQ ID NO 16
<211> LENGTH: 17
<212> TYPE: PRT
<213> ORGANISM: Artificial Sequence
<220> FEATURE:
<223> OTHER INFORMATION: FR-L2

<400> SEQUENCE: 16

Leu Ala Trp Tyr Gln Gln Lys Pro Gly Lys Ala Pro Lys Leu Leu Ile
1               5                   10                  15

Tyr


<210> SEQ ID NO 17
<211> LENGTH: 36
<212> TYPE: PRT
<213> ORGANISM: Artificial Sequence
<220> FEATURE:
<223> OTHER INFORMATION: FR-L3

<400> SEQUENCE: 17

Thr Leu Gln Ser Gly Val Pro Ser Arg Phe Ser Gly Ser Gly Ser Gly
1               5                   10                  15

Thr Glu Phe Thr Leu Thr Ile Ser Ser Leu Gln Pro Glu Asp Phe Ala
            20                  25                  30

Ser Tyr His Cys
        35


<210> SEQ ID NO 18
<211> LENGTH: 10
<212> TYPE: PRT
<213> ORGANISM: Artificial Sequence
<220> FEATURE:
<223> OTHER INFORMATION: FR-L4

<400> SEQUENCE: 18

Phe Gly Gly Gly Thr Lys Val Glu Ile Lys
1               5                   10


<210> SEQ ID NO 19
<211> LENGTH: 19
<212> TYPE: PRT
<213> ORGANISM: Artificial Sequence
<220> FEATURE:
<223> OTHER INFORMATION: signal peptide sequence

<400> SEQUENCE: 19

Met Gly Trp Ser Cys Ile Ile Leu Phe Leu Val Ala Thr Ala Thr Gly
1               5                   10                  15

Val His Ser


<210> SEQ ID NO 20
```

-continued

```
<211> LENGTH: 331
<212> TYPE: PRT
<213> ORGANISM: Artificial Sequence
<220> FEATURE:
<223> OTHER INFORMATION: amino acid seqeucne of transglutaminase

<400> SEQUENCE: 20

Asp Ser Asp Glu Arg Val Thr Pro Pro Ala Glu Pro Leu Asp Arg Met
1               5                   10                  15

Pro Asp Pro Tyr Arg Pro Ser Tyr Gly Arg Ala Glu Thr Ile Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Phe Phe Asp Glu Asp Lys Tyr Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Asp Ser Phe Asp Glu Ala Lys Gly Phe Gln Arg Ala Arg Asp
        115                 120                 125

Val Ala Ser Val Met Asn Lys Ala Leu Glu Asn Ala His Asp Glu Gly
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Asp Arg Asn Gly Gly Asn His Asp Pro Ser Lys
            180                 185                 190

Met Lys Ala Val Ile Tyr Ser Lys His Phe Trp Ser Gly Gln Asp Arg
        195                 200                 205

Ser Gly Ser Ser Asp Lys Arg Lys Tyr Gly Asp Pro Glu Ala Phe Arg
    210                 215                 220

Pro Asp Arg Gly Thr Gly Leu Val Asp Met Ser Arg Asp Arg Asn Ile
225                 230                 235                 240

Pro Arg Ser Pro Thr Ser Pro Gly Glu Ser Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Asp Gly Tyr Ser Asp
    290                 295                 300

Phe Asp Arg Gly Ala Tyr Val Val Thr Phe Val Pro Lys Ser Trp Asn
305                 310                 315                 320

Thr Ala Pro Asp Lys Val Thr Gln Gly Trp Pro
                325                 330
```